United States Patent
Hou et al.

(10) Patent No.: US 6,468,657 B1
(45) Date of Patent: Oct. 22, 2002

(54) CONTROLLABLE ION-EXCHANGE MEMBRANES

(75) Inventors: Zhizhong Hou; Pieter Stroeve, both of Davis, CA (US); Nicholas Abbott, Madison, WI (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/206,084

(22) Filed: Dec. 4, 1998

(51) Int. Cl.[7] .......................... B32B 5/16; A61L 5/103; G01N 33/53
(52) U.S. Cl. ............... 428/403; 427/2.11; 427/2.14; 427/217; 427/220; 428/404; 428/407; 428/699; 428/701; 428/702; 435/7.1; 435/7.7; 435/7.8; 435/7.9; 435/287.9; 436/72; 436/73; 436/80; 436/120; 436/127; 436/501; 514/495; 514/499; 514/501; 514/706; 514/770
(58) Field of Search ............... 428/403, 404, 428/407, 450, 457, 699, 701, 702; 427/2.11, 2.14, 217, 220; 435/7.1, 7.7, 7.8, 7.9, 287.1, 287.2, 287.9; 436/73, 72, 80, 120, 127, 501; 514/495, 499, 501, 706, 770

(56) References Cited

U.S. PATENT DOCUMENTS

| | | | |
|---|---|---|---|
| 4,246,091 A | | 1/1981 | Murayama et al. |
| 4,652,356 A | | 3/1987 | Oda et al. .................... 204/283 |
| 4,871,427 A | | 10/1989 | Kolesar, Jr. .................. 204/1 T |
| 4,872,958 A | | 10/1989 | Suzuki et al. ................. 204/98 |
| 4,931,498 A | * | 6/1990 | Pidgeon ..................... 525/54.1 |
| 4,964,972 A | * | 10/1990 | Sagiv et al. ................. 204/418 |
| 5,328,847 A | | 7/1994 | Case et al. ................... 435/291 |
| 5,472,881 A | * | 12/1995 | Beebe et al. .................... 436/94 |
| 5,660,892 A | | 8/1997 | Robbins et al. ............. 427/537 |
| 5,728,431 A | * | 3/1998 | Bergbreiter et al. ..... 427/388.1 |
| 5,919,576 A | * | 7/1999 | Hui et al. .................... 428/545 |
| 5,922,550 A | * | 7/1999 | Everhart et al. ........... 435/7.21 |
| 5,942,388 A | * | 8/1999 | Willner et al. ................. 435/6 |
| 5,942,397 A | * | 8/1999 | Tarlov et al. ................. 435/6 |
| 6,013,855 A | * | 1/2000 | McPherson et al. .......... 623/11 |

OTHER PUBLICATIONS

Elmidaoui et al., "Synthesis and Characterization of New Ion–Exchange Membranes" *J. App. Polym Sci.* 42:2551–2561 (1991).

Breitbach et al., "Heterogeneous functionalizing of polysulfone membranes" *Angew Makromol. Chem.* 184:183–196 (1991).

Menon et al., "Fabrication and Evaluation of Nanoelectrode Ensembles" *Anal. Chem.* 67:1920–1928 (1995).

Nishizawa et al., "Metal Nanotubule Membranes with Electrochemically Switchable Ion–Transport Selectivity" *Science* 268:700–702 (1995).

Jirage et al., "Nanotubule–Based Molecular–Filtration Membranes" *Science* 278:655–658 (1997).

Yu et al., "Electochemical Behavior of Azobenzene Self – Assembled Monolayers on Gold" *Langmuir* 12:2843–2848 (1996).

(List continued on next page.)

Primary Examiner—Hoa T. Le
(74) Attorney, Agent, or Firm—Townsend and Townsend and Crew LLP

(57) ABSTRACT

Multilayered porous materials are formed by coating a porous substrate with a metal and adsorbing an organic layer comprising a recognition moiety onto the metal film. The recognition moiety interacts with an analyte of interest allowing for its detection, purification, etc. Suitable recognition moieties can be selected from a range of species including, small molecules, polymers and biomolecules and the like. The novel porous materials of the invention can be utilized in an array of methods including, ion-exchange, ion-selective ion-exchange, assays, affinity dialysis, size exclusion dialysis and the like.

71 Claims, 4 Drawing Sheets

OTHER PUBLICATIONS

Kumano et al., "Photoresponsive Permeation Characteristics of a Ternary Composite Membrane of Polymer/Artificial Lipid/Azobenzene Derivative" *Polymer J*. 16(6):461–470 (1984).

Seki et al., "'Command Surfaces' of Langmuir—Blodgett Films. Photoregulations of Liquid Crystal Alignment by Molecularly Tailored Surface Azobenzene Layers" *Langmuir* 9:211–218 (1993).

Sekkat et al., "A 'Smart' Ultrathin Photochromic Layer" *Langmuir* 11:2856–2859 (1995).

Lakshmi et al., "Enantioseparation using apoenzymes immobilized in a porous polymeric membrane" *Nature* 388:758–760 (1997).

Noble et al., "Facilitated Transport Membrane Systems" *Chem. Eng. Progr.* 85:58–70 (1989).

Noble, "Generalized microscopic mechanism of facilitated transport in fixed site carrier membranes" *J. Membr. Sci.* 75:121–129 (1992).

* cited by examiner

CONTROLLABLE ION-EXCHANGE MEMBRANES

CROSS-REFERENCE TO RELATED APPLICATIONS

This application is related to U.S. patent application Ser. No. 09/205,750, filed on an even date, the teachings of which are incorporated herein by reference for all purposes.

STATEMENT AS TO RIGHTS TO INVENTIONS MADE UNDER FEDERALLY SPONSORED RESEARCH AND DEVELOPMENT

This work was partially supported by the National Science Foundation MRSEC Program, (DMR-9400354) and the CAREER Program (CTS-9410147). Support was also received from the Office of Naval Research, Presidential Early Career Award for Science and Engineering (N00014-97-1-0703).

BACKGROUND OF THE INVENTION

Ion-exchange membranes play an important role in separation and purification processes. These membranes generally consist of either highly swollen gels or microporous structures with fixed charges derived from ionizable functional groups localized at the pore walls (Strathmann, H., In *Synthetic Membranes: Science, Engineering and Applications;* Bungay, P. M.; Lonsdale, H. K.; de Pinho, M. N., Eds.; NATO ASI Series C: Mathematical and Physical Sciences Vol. 181; D. Reidel Publishing Company: Dordrecht, Holland, (1986), pp 1–37). A membrane that contains fixed positive charges is called an anion-exchange membrane, and a membrane bearing fixed negative charges is called a cation-exchange membrane. The general purpose of ion-exchange membranes is not to exchange ions but to transmit them in a controlled way (Meares, P., In *Mass Transfer and Kinetics of Ion Exchange;* Liberti, L.; Helffefich, F. G., Eds.; NATO ASI Series E: Applied Science No. 71; Martinus Nijhoff Publishers, The Hague, The Netherlands, (1983); pp 329–366). Co-ions (i.e., ions with the same charges as the fixed charges) are excluded from the pores, whereas counterions (i.e., ions with opposite charges to the fixed charges) selectively transport across the membrane. Ion-exchange membranes have been used in the following processes, classified by the driving forces of transport of ions (Meares, P., In *Mass Transfer and Kinetics of Ion Exchange;* Liberti, L.; Helffefich, F. G., Eds.; NATO ASI Series E: Applied Science No. 71; Martinus Nijhoff Publishers, The Hague, The Netherlands, (1983); pp 329–366): (a) for electrical driving forces, desalination, demineralization, concentration of solutions, exchange of ions, and oxidation-reduction (e.g., chlor-alkali processes); (b) for driving forces of concentration gradient, diffusion dialysis, solid electrolytes in batteries, and ion-selective electrodes, (c) for driving forces of pressure, reverse osmosis and piezodialysis.

The most common functional groups in cation-exchange membranes are sulfonic acid ($SO_3H$) and carboxylic acid (—COOH) groups. The Nafion brand perfluorosulfonated polymer membranes (Meares, P., In *Mass Transfer and Kinetics of Ion Exchange;* Liberti, L.; Helffefich, F. G., Ed.; NATO ASI Series E: Applied Science No. 71; Martinus Nijhoff Publishers, The Hague, The Netherlands, (1983); pp 329–366; Yeager, H. L. et al., In *Perfluorinated Ionomer Membranes;* Yeager, H. L.; Eisenberg, Eds.; ACS Symposium Series 180; American Chemical Society: Washington, D.C., (1982); pp 1–6) are an example of the first type. These membranes were developed by E. I. du Pont de Nemours & CO. during the 1960's and are still extensively used in industry. The perfluoro-sulfonic acid is ionized at normal pH values because of their low $pK_a$ values (<1) (Seko, M. et al., ibid.; pp 365–410). In the seventies some Japanese companies (Asahi Chemical Co., Asahi Glass Co., and Tokuyama Soda Co.) developed perfluorocarboxylated membranes that contain carboxylic acid groups (Seko, M. et al., ibid.; pp 365–410; Sata, T. et al., ibid.; pp 411–425; Ukihastfi, H. et al., ibid.; pp 427–451; Sato, K. et al., *PolymerJ.,* 23, 1991, 531–540). Although the perfluorocarboxylic acid has a higher $pK_a$ (2–3), it can be nearly completely ionized even in weakly acidic environments. Other functional groups such as phosphonic acid (—$PO_3H_2$) and sulfonamide (—$SO_2NH_2$) are sometimes used but are less practical.

The functional groups in anion-exchange membranes are usually quaternary ammonium [—$N^+(CH_3)_3$] and to a lesser extent quaternary phosphonium [—$P^+(CH_3)_3$] and tertiary sulfonium [—$S^+(CH_3)_2$]. Anion-exchange membranes are frequently less stable than cation-exchange membranes because the basic groups are inherently less stable than the acidic groups (Strathmann, H. In *Synthetic Membranes: Science, Engineering and Applications;* Bungay, P. M.; Lonsdale, H. K.; de Pinho, M. N., Eds.; NATO ASI Series C: Mathematical and Physical Sciences Vol. 181; D. Reidel Publishing Company: Dordrecht, Holland, (1986); pp 1–37).

Conventional ion-exchange membranes are generally produced by: (a) polymerization (condensation or addition) of ionogenic monomers; (b) introduction of ionizable groups into a polymer film by grafting and/or chemical treatment; or (c) heterogeneously dispersing an ion exchange material into a binder polymer matrix.

The Nafion perfluorosulfonated membranes are copolymers of tetrafluoroethylene and perfluorovinyl ethers containing sulfonic acid groups (Yeager, H. L. et al., In *Perfluorinated Ionomer Membranes;* Yeager, H. L.; Eisenberg, Eds.; ACS Symposium Series 180; American Chemical Society: Washington, DC, (1982); pp 1–6). Synthesis of perfluorocarboxylated membranes is similar, but the sulfonic acid groups in perfluorovinyl ethers are replaced by carboxylic acid groups (Seko, M. et al., ibid.; pp 365–410; Sata, T. et al., ibid.; pp 411–425; Ukihastfi, H. et al., ibid.; pp 427451; Sato, K. et al., *PolymerJ.,* 23, 1991, 531–540).

Perfluorinated ionomer (i.e., ion-containing polymer) membranes constitute a significant portion of ion-exchange membranes and are extensively used in the chlor-alkali industry (Dotson, R. et al., In *Perfluorinated Ionomer Membranes;* Yeager, H. L. Eisenberg, Eds.; ACS Symposium Series 180; American Chemical Society: Washington, D.C., 1982, pp 311–364). Composite membranes are sometimes utilized to improve the separation performance. An exemplary composite membrane has layers of both sulfonic acid and carboxylic acid polymers bound together to improve permselectivity (Sato, K. et al., *PolymerJ.,* 23, 1991, 531–540). Composite layers having a layer of polyanion adsorbed onto a cation-exchange membrane have been prepared. Such membranes could prevent the precipitation of hydroxides and simplify the control of membrane fouling (Meares, P., In *Mass Transfer and Kinetics of Ion Exchange;* Liberti, L.; Helffefich, F. G., Eds,; NATO ASI Series E: Applied Science No. 71; Martinus Nijhoff Publishers, The Hague, The Netherlands, (1983); pp 329–366). Recent development in synthesis of ion-exchange membranes focus on new polymerization processes, such as radiation induced grafting (Chakravorty, B. et al., *Membr. Sci.* 1989, 41, 155–161; Gineste, J.-L. et al., *Polym. Sci.:* Part A: *Polym. Chem.* 1993, 31, 2969–2975) and copolymerization, (,G. K. et al., *Membr. Sci.* 1992, 68, 133–140) plasma polymerization of ionomer films (Brumlik, C. J. et al., *Electrochem. Soc.* 1994, 141, 2273–2279), deposition of thin polymer film by plasma polymerization (Osada, Y. In *Membrane Science and Technology;* Osada, Y.; Nakagawa, T., Eds.; Marcel Dekker, Inc.: New York, 1992; pp 167–201), and grafting of functional groups on polymers treated by ozonization Elmidaoui, A. et al., *Appl. Polym. Sci.* 1991, 42, 2551–2561).

In conventional ion-exchange membranes prepared by polymer chemistry, ion transport operates in a gel phase formed by sorption of water and swelling of the membrane due to the hydrophilic functional groups on the polymer backbone (Leddy, J. J. In *Synthetic Membranes;* Chenowetb, M. B., Ed.; MMI Press Symposium Series; Harwood Academic Publishers: London, 1986; pp 119–128). The size of pores, however, is difficult to control and there can be undesired transport of water and co-ions across the membrane, leading to poor perm-selectivity. Perfluorocarboxylated membranes are believed to have higher permselectivity than the Nafion membranes due to less uptake of water by the carboxylic groups than by the sulfonic groups (Sato, K. et al., *PolymerJ.*, 23, 1991, 531–540).

Ion-exchange membranes with a porous structure were recently prepared by several techniques to offer membranes with both suitable pore sizes and good ion exchange capacity. These techniques include oxidative etching of gel-like ion-exchange membranes (Mizutani, Y. et al., *J. Appl. Polym. Sci.* 1990, 39, 1087–1100), chemical modification of preformed ultrafiltration membranes (Breitbach, L. et al., *Angew. Makromol. Chem.* 1991, 184, 183–196), and removal of inorganic fillers from a polymer blend and modification of the polymer matrix (Bryjak, M. et al., *Angew. Makromol. Chem.* 1992, 200, 93–108). Using those techniques, however, it is not flexible to introduce various functional groups and the pore sizes of the membranes are usually not uniform.

Martin et al. recently reported electroless deposition of gold onto the pore walls in polycarbonate track-etched (PCTE) filtration membranes (Menon, V. P. et al., *Anal. Chem.* 1995, 67, 1920–1928; Nishizawa, M. et al., *Science* 1995, 268, 700–702; Jirage, K. B. et al., *Science* 1997, 278, 655–658). Such gold-coated membranes have unique properties. Application of a positive or a negative electrical potential to gold resulted in anion or cation selectivity, respectively and the ion selectivity was reversibly altered by manipulation of the applied electrical potential (Nishizawa, M. et al., *Science* 1995, 268, 700–702).

Self-assembled monolayers formed with ω-substituted alkanethiols on the surface of gold have been used as model surfaces in a number of past studies of the interactions of proteins with surfaces (Spinke et al., *Langumuir,* 9: 1821 (1993); Willner et al.,*J. Am. Chem. Soc.,* 114: 10965 (1992); Song et al., *J. Phys, Chem.,* 97: 6564 (1993); Mrksich et al., *J. Am. Chem. Soc.,* 117: 12009 (1995)). For example, multilayer systems based on biotinylated alkanethiols and streptavidin have been used in schemes for the immobilization of Fab fragments of antibodies on surfaces (Spinke et al., *Langumuir,* 9: 1821 (1993)), and SAMs formed from NHS-activated disulfidies have been used to form enzyme-based electrodes by covalent immobilization of glutathione reductase (Willner et al., *J. Am. Chem. Soc.,* 114: 10965 (1992)). Cytochrome c, when adsorbed to SAMs formed from mercaptoundecanoic acid, has also been shown to be active and to possess a formal potential nearly identical to that of cytochrome c bound to physiological membranes (Song et al., *J. Phys, Chem.,* 97: 6564 (1993)).

Whereas, investigations such as those described above have firmly established the use of SAMs for studies of specific interactions between proteins and surfaces, mixed SAMs formed from hydrophobic (methyl-terminated) and hydrophilic (hydroxyl-, oligo(ethylene glycol)-terminated) alkanethiols have also been used as model surfaces in studies of non-specific adsorption of proteins onto surfaces. Whitesides and coworkers, for example, have reported a study of the non-specific adsorption of fibrinogen, lysozyme, pyruvate kinase and RNAse to mixed SAMs (Prime et al.,*J. Am. Chem. Soc.,* 115: 10714 (1993); Prime et al., *Science,* 252: 1164 (1991)). By using ellipsometry, SAMs formed from oligo(ethylene glycol)-terminated alkanethiols were shown to resist irreversible adsorption of these proteins.

Surfaces prepared by the chemisorption of organosulfur compounds on evaporated films of gold are not limited to the alkanethiols. Self-assembled monolayers formed from perfluorinated organosulfur compounds have also been reported. See, Lenk et al., *Langmuir,* 10: 4610 (1994); Drawhorn et al., *J. Phys. Chem.,* 99: 16511 (1995). These surfaces, too, can be highly ordered, although, interestingly, the origin of the order within the monolayer is largely intramolecular and contrasts, therefore, to monolayers formed from alkanethiols (where the order largely reflects the cohesive intermolecular dispersion force). Steric interactions between adjacent fluorine atoms of a perfluorinated chain cause the chain to twists itself into a rigid, helical conformation. That is, an isolated perfluoro chain is stiff, as compared to an aliphatic chain. Because perfluorinated chains have larger cross-sectional areas than alkanethiols, monolayers formed on gold from perfluorinated thiols are not tilted from the normal to the same degree as alkanethiols. See, Drawhorn et al., *J. Phys. Chem.,* 99: 16511 (1995). Estimates by IR studies place the tilt of the perfluorinated chains at 0–10°. Because perfluorinated chains within SAMs on Au(111) are not tilted to the same degree as the alkanethiols, their surfaces are not expected to possess domains formed from regions of monolayer with different tilt directions (as occurs with monolayers formed from alkanethiols).

Gold-coated PCTE membranes were recently reported. See, Nishizawa, M. et al., *Science* 1995, 268, 700–702). These membranes were derivatized with 1-propanethiol to protect the gold from adventitious binding of anions (such as $Cl^-$, $Br^-$, and $I^-$) presented in external solutions. These workers, however, did not investigate whether 1-propanethiol (or any alkanethiol) formed close-packed monolayers on the electroless gold coated membrane under the conditions used to prepare the membranes. Further, no suggestion was made to derivatize the 1-propanethiol layer with ionic or other groups to impart functionality and recognition properties to the membranes.

Easily prepared and characterized membranes that are capable of presenting a wide range of recognition groups (ionic groups, metal, complexing agents, biomolecules, and the like), pore sizes, surface charges and surface hydrophilicity/hydrophobicity would represent a significant advance in membrane science. Quite surprisingly, the present invention provides such membranes and methods of making and using these membranes.

SUMMARY OF THE INVENTION

It has now been discovered that membranes coated with metal films can be functionalized with SAMs (mixed and homogeneous) formed from organic groups bearing recognition moieties. Because a wide range of recognition moieties can be easily introduced onto surfaces by these methods, these membranes are useful for a range of purification methods and assays.

Thus, in a first aspect, the present invention provides a multilayered material comprising:
(a) a porous substrate;
(b) a metal film adhered onto said porous substrate;
(c) an organic layer attached to said metal film, said organic layer comprising a recognition moiety.

In a second aspect, the invention provides a multilayered material comprising:
(a) a polycarbonate track-etched substrate;
(b) a metal film adhered onto said substrate; and
(c) an organosulfur layer attached to said metal film, said organosulfur layer comprising a recognition moiety.

In a third aspect, the present invention provides an ion exchange medium comprising:
(a) a porous substrate;
(b) a metal film adhered onto said substrate; and
(c) an organic layer attached to said metal film, said organic layer comprising a recognition moiety that interacts with said ion.

In a fourth aspect, the present invention provides a method for removing an ion from a fluid, said method comprising:
(a) contacting said fluid with an ion exchange medium comprising:
 (i) a porous substrate;
 (ii) a metal film adhered onto said substrate; and
 (iii) an organic layer attached to said metal film, said organic layer comprising a recognition moiety that interacts with said ion.

In a fifth aspect, the present invention provides a method for isolating a molecule from other molecules by affinity dialysis comprising:
(a) contacting the molecule with a multilayered porous material comprising;
 a porous substrate;
 a metal film adhered onto the substrate; and
 an organic layer attached to the metal film, the organic layer comprising a recognition moiety.
(b) forming a complex between the recognition moiety and the molecule.

In a sixth aspect, the present invention provides a method of isolating a first molecule from a second molecule by size exclusion dialysis, comprising:
(a) contacting the first and second molecule with a multilayered porous material comprising;
 a porous substrate;
 a metal film layered onto the substrate;
 a hydrophilic polymer attached to the metal film; and
 passing the first molecule through the porous material while the second molecule is substantially retained thereby.

In a seventh aspect, the present invention provides a method for determining the presence or amount of an analyte in a test sample comprising:
(a) contacting the test sample with a multilayered porous material comprising;
 a porous substrate;
 a metal film layered onto the substrate;
 an organic layer adhered to the metal film, the organic layer comprising a recognition moiety;
(b) forming a complex between the recognition moiety and the analyte; and
(c) detecting the analyte.

In an eighth aspect, the invention provides a method of producing a multilayered porous material comprising:
(a) contacting a porous substrate with a metal plating means to form a porous substrate having a metal film adhered thereto;
(b) contacting said porous substrate having a metal film adhered thereto with a plurality of organic molecules that associate with said metal film, wherein at least a portion of said plurality of organic molecules comprise a member selected from the group consisting of recognition moieties, reactive groups, protected reactive groups and combinations thereof.

In a ninth aspect, the present invention provides a drug delivery device comprising:
(a) a porous substrate;
(b) a metal film adhered onto said substrate;
(c) an organic layer attached to said metal film, said organic layer containing a recognition moiety; and
(d) a drug moiety reversibly associated with said recognition moiety.

Additional objects and advantages of the invention will be apparent to those of skill in the art from the detailed description and the examples that follow.

DETAILED DESCRIPTION OF THE INVENTION AND THE PREFERRED EMBODIMENTS

Abbreviations and Definitions

Figure 1:
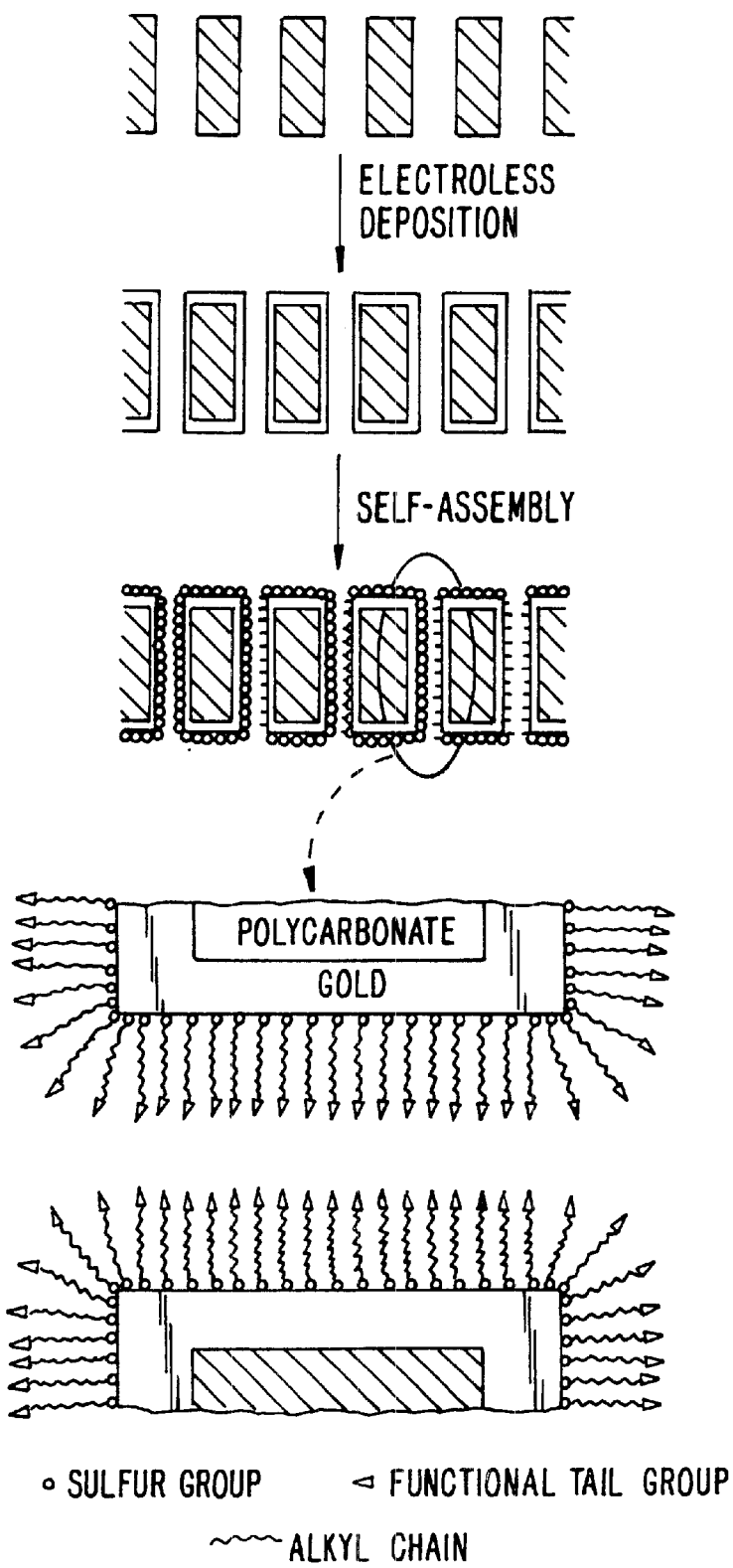
FIG. 1 is a schematic illustration of the membrane prepared by electroless deposition of gold on a PCTE membrane followed by self-assembly of functionalized thiols.

SAM, self assembled monolayer.

The term "attached," as used herein encompasses interactions including, but not limited to, covalent bonding, ionic bonding, chemisorption, physisorption and combinations thereof.

The term "fluid" refers to pure liquids, solutions, suspensions, colloids, gases, vapors, mixtures of two or more of these "fluids" and the like.

The term "independently selected" is used herein to indicate that the groups so described can be identical or different.

The term "alkyl" is used herein to refer to a branched or unbranched, saturated or unsaturated, monovalent hydrocarbon radical having from 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon of the alkyl moiety. Additionally, these groups may be pendent from, or integral to, the alkyl chain.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

The term "arylalkyl" is used herein to refer to a subset of "aryl" in which the aryl group is attached to another nucleus by an alkyl group as defined herein.

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached to another nucleus by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —H.

The term "amino" is used to describe primary amines, R—$NH_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and are as described herein for "alkyl groups."

As used herein, the term "acylamino" describes substituents of the general formula RC(O)NR', wherein R' is a lower alkyl group and R represents another organic radical.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e. RC(O)OR' or R'OC(O)R, respectively, wherein R comprises the portion of the ester attached either directly or through an intermediate hydrocarbon chain to another nucleus.

As used herein, the term "aryloxy" denotes aromatic groups which are linked to another nucleus directly through an oxygen atom. This term encompasses "substituted aryloxy" moieties in which the aromatic group is substituted as described above for "substituted aryl."

As used herein "aryloxyalkyl" defines aromatic groups attached, through an oxygen atom to an alkyl group, as defined herein. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and are alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to another nucleus.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to another nucleus.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another nucleus.

"Organosulfur," as used herein, encompasses, organothiols, -sulfides, and -disulfides.

"Alkylsulfur," as used herein, encompasses, thiols, sulfides, disulfides and derivatives of these compounds wherein the alkyl group is substituted as described above for "substituted alkyl."

A. Introduction

The present invention provides a broad range of novel materials. The materials are porous materials such as membranes that, unlike presently available membranes, have a structure that allows many of their properties to be tailored by variations in the components used at the various stages of assembly of these materials. In addition to providing the materials themselves, the present invention provides methods for using and making these novel materials.

Thus, in a first aspect, the present invention provides a multilayered material comprising:

a multilayered porous material comprising:
(a) a porous substrate;
(b) a metal film adhered onto said porous substrate; and
(c) an organic layer attached to said metal film, said organic layer comprising a recognition moiety.

Metals can be plated onto membrane substrates using sputtering, controlled vapor deposition or electroless plating techniques to produce membranes with a metal layer substantially coating the membrane surface. The metal coating generally comprises a metal that forms a bond or intimate association (e.g., chemisorption, physisorption) with an organic molecule, such as an organosulfur (e.g., alkylthiol, sulfide, disulfide) with which the metal coated membranes are surface-functionalized.

The organic layer comprises a recognition moiety, which is a molecule or portion of a molecule that interacts with an analyte. The interaction can be either attractive or repulsive. In an exemplary attractive interaction, the recognition moiety will assist the entry of the analyte into the pores of the porous material. In an exemplary repulsive interaction, the analyte will be excluded from the pores of the porous material. Useful recognition moieties can be, for example, biomolecules (e.g., antibodies, antigens, carbohydrates, nucleic acids, peptides, enzymes and receptors), organic groups (e.g., amines, carboxylic acids, drugs, chelating agents, crown ethers, cyclodextrins and combinations thereof), metal chelates and organometallic moieties. In addition to the molecule bearing the recognition moiety, the organic layer can be mixed with other species that do not bear recognition moieties.

Certain commercially-available, well-characterized membranes have excellent properties and provide a good entry point for developing new membranes with useful characteristics.

Thus, in a second aspect, the invention provides a multilayered material comprising:

a multilayered porous material comprising:
(a) a polycarbonate track-etched substrate;
(b) a metal film adhered onto the substrate; and
(c) an organosulfur layer attached to said metal film, the organosulfur layer comprising a recognition moiety.

Although the porous materials of the invention can bear any of a range of recognition moieties, certain useful materials will bear recognition moieties that are useful for ion-exchange or ion-selective ion-exchange of charged species. The materials of the invention are ideally structures for such uses.

Thus, in a third aspect, the present invention provides an ion exchange medium comprising:

(a) a porous substrate;
(b) a metal film adhered onto said substrate; and
(c) an organic layer attached to said metal film, said organic layer comprising a recognition moiety that interacts with said ion.

In addition to new materials and useful methods utilizing these materials, the present invention provides straightforward methods for assembling these materials. Solution-phase metal plating methods can be used to coat porous membrane substrates with films consisting of single metals, alloys and composites. The film coated membranes are functionalized with an organic layer, generally formed from substituted organosulfur molecules, however, any organic layer that attaches to the film can be used. At least one component of the organic layer will bear a recognition moiety that interacts with a molecule of interest, referred to herein as an "analyte." Because a wide range of recognition moieties can be easily introduced onto surfaces by a wide range of methods, these membranes are useful for a range of purification methods and assays.

The materials, methods, additional aspects and preferred embodiments of the present invention are discussed in greater detail in the sections that follow.

Porous Substrates

Porous substrates that are useful in practicing the present invention can be made of practically any physicochemically stable material. Substrates can be selected from the group consisting of optically opaque substrates, optically transparent substrates, insulating substrates, conducting substrates, semiconducting substrates, magnetic substrates and combinations thereof.

Useful porous substrates are not limited to a pore size or range of pore sizes. The choice of an appropriate pore size for a given application will be apparent to those of skill in the art. In certain preferred embodiments, the substrate has a pore diameter of from about 0.005 micrometer to about 25 micrometers. In other preferred embodiments, the substrate has a diameter of from about 0.01 micrometer to about 1 micrometer.

Exemplary substrate materials include, but are not limited to, inorganic crystals, inorganic glasses, inorganic oxides, metals, organic polymers and combinations thereof.

In a presently preferred embodiment, the substrate is track-etched.

B.1. Inorganic Crystals and Glasses

Inorganic crystals and inorganic glasses that are appropriate for substrate materials include, for example, LiF, NaF, NaCl, KBr, KI, $CaF_2$, $MgF_2$, $HgF_2$, BN, $AsS_3$, ZnS, $Si_3N_4$ and the like. The crystals and glasses can be prepared by art standard techniques. See, for example, Goodman, Crystal Growth Theory and Techniques, Plenum Press, New York, 1974. Alternatively, the crystals and glasses can be purchased commercially (e.g., Fischer Scientific, Duke Scientific Corporation, Palo Alto, Calif.). The crystals and glasses can be the sole component of the substrate or they can be coated with one or more additional substrate components. Thus, it is within the scope of the present invention to utilize crystals and/or glasses coated with, for example one or more metal films or a metal film and an organic polymer. Additionally, a crystal and/or glass can constitute a portion of a substrate that contacts another portion of the substrate made of a different material, or a different physical form (e.g., a glass) of the game material. Other useful substrate configurations utilizing inorganic crystals and/or glasses will be apparent to those of skill in the art.

B.2. Inorganic Oxides

Inorganic oxides can also form a substrate of the device of the present invention. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), silica, quartz, $In_2O_3$, $SnO_2$, $PbO_2$, silicone polymers and the like. The inorganic oxides can be utilized in a variety of physical forms such as powders, glasses, crystals, resins, plastics and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed and deposited on a support such as a porous glass, polymer or metal sheet. Further, a layer of one or more inorganic oxides can be intercalated between two other substrate layers (e.g., metal-oxide-metal, metal-oxide-crystal). Appropriate inorganic oxide materials can be prepared or, alternatively, they can be purchased from commercial sources (e.g., Duke Scientific Corporation, Palo Alto, Calif.).

Inorganic oxides membranes are resistant to aggressive chemicals like acids, alkalines and solvents. These membranes are also resistant to abrasive suspensions and temperature fluctuations. Methods of making inorganic oxide membranes are known to those of skill in the art. Additionally, appropriate membranes are available commercially from sources such as Schumacher Umwelt- und Trenntechnik GmbH (Crailsheim, Germany). The membranes are available in pore sizes between 0.005–1.2 micrometers and in at least eight different geometries.

In a preferred embodiment, the inorganic oxide is a member selected from the group ZnO, $TiO_2$, $Fe_2O_3$, $Al_2O_3$, $ZrO_2$, $ZrO_2/TiO_2$, $CeO_2$, $SnO_2$, CuO, $Cr_2O_3$, $SiO_2$ and combinations thereof.

B.3. Metals

Metals are also of use as porous substrates in the present invention. The metal can be used as a crystal or an amorphous material, such as a powder. When a powder is used, it will preferably have been formed into a desired configuration by a method such as casting, pressing, molding and the like. Appropriate metal membranes are available from a variety of sources such as Alternburger electronic GmbH (Seelbach, Germany). As most of the surface characteristics of the metal membrane will be masked by its metallic coating layer, there are essentially no limitations on the types identity of metal that can be used in the present invention. The metal membranes can be selected for desirable physical properties such as density, magnetic characteristics, conducting or insulating characteristics, heat capacity and the like.

In preferred embodiments, the metal substrate is a member selected from the group of nickel, copper, silver, gold, platinum, palladium and combinations thereof.

B.4. Organic Polymers

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysaccharides (e.g., dextran derivatives), polysilanes, fluorinated polymers, epoxies, polyethers and phenolic resins.

Many commercially available polymer- or resin-based membranes can also be used in practicing the present invention. Moreover, commercially available membranes having well-defined pore sizes are available over a wide pore size range and composed of a number of different materials.

Presently preferred polymer- or resin-based membranes include those constructed of polymers selected from the group of polypropylene, nylon, fluorocarbon, polyester, polyethylene, polysulfone, polyether sulfone, cellulose, cellulose ester, ethyl vinyl acetate, polycarbonate, polyaramide, polyimide and combinations thereof.

C. Metal Coatings

Metals that are presently preferred as coatings for particulate substrates include, but are not limited to, gold, silver, platinum, palladium, nickel and copper. Silver and gold are preferred, gold being particularly preferred. Other useful metal coatings are composite materials that form an association with the sulfur atom(s) of thiols, sulfides and/or disulfides (e.g., ZnSe).

The metal coating can be either continuous or discontinuous. Further, the thickness of the metal layer can remain constant or it can vary over the surface of the porous substrate. In one embodiment, more than one metal is used. The more than one metal can be present as an alloy, they can be formed into a layered "sandwich" structure, or they can be laterally adjacent to one another. In a preferred embodiment, where more than one metal layer is used, the outermost metal is gold. In a particularly preferred embodiment the metal used is gold layered on silver, more preferably gold layered on silver which has been layered onto a membrane activated by the adsorption of tin.

A wide range of art-recognized techniques leading to the deposition of a metal layer onto a substrate are appropriate for use in practicing the present invention, including sputtering, controlled-vapor deposition and electroless plating. In a preferred embodiment, the metal is deposited by an electroless plating method.

Metals can be plated onto membranes using electroless plating techniques to produce membranes with a metal layer substantially coating the membrane surface. In a particularly preferred embodiment, the metal coating comprises a metal that forms a bond or intimate association (e.g., chemisorption, physisorption) with an organic molecule, such as an organosulfur (e.g., alkylthiol, sulfide, disulfide). The metal coated membranes can be surface-functionalized with SAMs (mixed and homogeneous) formed from organosulfur moieties.

Due to the extensive literature on their synthesis and characterization and the commercial availability of many species having useful structures and properties, ω-substituted alkylsulfur compounds are preferred as components of the organic layer.

D. Organic Layers

A wide variety of organic layers are useful in practicing the present invention. These organic layers can comprise monolayers, bilayers and multilayers. Furthermore, the organic layers can be attached by covalent bonds, ionic bonds, coordinating bonds, physisorption, chemisorption and the like, including, but not limited to, hydrophobic interactions, hydrophilic interactions, van der Waals interactions and the like.

In a presently preferred embodiment, organic layer components which form self-assembled monolayers are used.

In the discussion that follows, self-assembled monolayers are utilized as an exemplary organic layer. This use is not intended to be limiting. It will be understood that the various configurations of the self-assembled monolayers and their methods of synthesis, binding properties and other characteristics are equally applicable to each of the organic layers of use in the present invention.

D.1 Self-Assembled Monolayers ("SAMs")

Self-assembled monolayers are generally depicted as an assembly of organized, closely packed linear molecules. There are two widely-used methods to deposit molecular monolayers on solid substrates; Langmuir-Blodgett transfer and self-assembly. Additional methods include techniques such as depositing a vapor of the monolayer precursor onto a substrate surface. Each of these methods is appropriate for use in practicing the present invention.

The composition of a SAM useful in the present invention, can be varied over a wide range of compound structures and molar ratios. In one embodiment, the SAM is formed from only one compound. In a presently preferred embodiment, the SAM is formed from two or more compounds. In another preferred embodiment, the organic layer comprises a plurality of compounds, each compound comprising a moiety that associates with the metal film.

In preferred embodiments, the organic layer and/or the recognition moiety undergoes a change in state upon being exposed to certain conditions. In general, the change of state will alter the pore size or the species selectivity of the pores to, for example, exclude a previously allowed species from the pores or vice-versa. Organic layer and/or recognition moiety states that can undergo alteration include, for example, steric bulk, polarity, conformation and redox potential. Conditions that can be manipulated to produce these and other changes in state include, for example, fluid redox potential, fluid ionic strength, fluid pH, application of external fields (electrical, magnetic, etc.), light (UV, IR, etc.).

In one exemplary embodiment, the organic layer and/or recognition moiety comprises an azobenzene or other group that undergoes a change of state under the influence of external conditions such as changes in pH, ionic strength, temperature and incident light. In other embodiments, the group undergoes a change of state in response to applied electrical or magnetic fields.

In yet a further preferred embodiment, the organic layer comprises a group having the structure:

wherein $R^1$ is a linking group between sulfur and $X^1$; $X^1$ is a member selected from the group consisting of H, halogen, recognition moieties, hydrophilic polymers and combinations thereof; and n is a number between 1 and 50.

In a preferred embodiment, the SAM component bearing $X^1$ is attached directly and essentially irreversibly via a "stable bond" to the surface of the substrate. A "stable bond", as used herein, is a bond which maintains its chemical integrity over a wide range of conditions (e.g., amide, carbamate, carbon-carbon, ether, etc.). In another preferred embodiment the SAM component bearing the recognition moiety comprises a "cleaveable bond". A "cleaveable bond," as used herein, is a bond which undergoes scission under conditions which do not degrade other bonds in the recognition moiety-analyte complex. Cleaveable bonds include, but are not limited to, disulfide, imine, carbonate and ester bonds.

Exemplary applications wherein it is preferred that the molecule ("analyte") that interacts with $X^1$ remains tethered to the surface include, but are not limited to, quantitating or measuring a property of the analyte while it is tethered to the surface. Alternatively, the material of the invention can be used to remove an analyte from a fluid such as a liquid or vapor mixture to purify or partially purify that mixture or the analyte. Many other applications wherein the analyte remains tethered to the surface will be apparent to those of skill in the art.

Preferred $R^1$ groups with "stable" bonds include $R^1$ groups which are members selected from the group consisting of alkyl, substituted alkyl, aryl, arylalkyl, substituted aryl, substituted arylalkyl, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups. Further preferred stable $R^1$ groups are members selected from the group consisting of alkyl and substituted alkyl groups.

Exemplary applications wherein the analyte or $X^1$-analyte complex is removable from the surface include, but are not limited to, purification of an analyte, synthesis of a molecule on the material of the invention and regeneration of the material of the invention.

Many cleaveable groups are known in the art. See, for example, Jung et al., *Biochem. Biophys. Acta,* 761: 152–162 (1983); Joshi et al., *J. Biol. Chem.,* 265: 14518–14525 (1990); Zarling et al., *J. Immunol.,* 124: 913–920 (1980); Bouizar et al., *Eur. J. Biochem.,* 155: 141–147 (1986); Park et al., *J. Biol. Chem.,* 261: 205–210 (1986); Browning et al., *J. Immunol.,* 143: 1859–1867 (1989). Exemplary cleaveable moieties can be cleaved using light, heat or reagents such as thiols, hydroxylamine, bases, periodate and the like. Preferred cleaveable groups comprise a cleaveable moiety which is a member selected from the group consisting of disulfide, ester, imide, carbonate, nitrobenzyl, phenacyl and benzoin groups.

When two or more structurally distinct moieties are used as components of the SAMs, the components can be contacted with the substrate as a mixture of SAM components or, alternatively, the components can be added sequentially. In those embodiments in which the SAM components are added as a mixture, the mole ratio of a mixture of the components in solution generally results in the same ratio in the mixed SAM. Depending on the manner in which the SAM is assembled, the two components do not phase segregate into islands. See, Bain et al., *J. Am. Chem. Soc.,* 111: 7164 (1989). This feature of SAMs can be used to immobilize recognition moieties or bulky modifying groups in such a manner that certain interactions, such as steric hindrance, between these molecules is minimized.

The individual components of the SAMs can also be bound to the substrate in a sequential manner. Thus, in one embodiment, a first SAM component is attached to the substrate's surface by "underlabeling" the surface functional groups with less than a stoichiometric equivalent of the first component. The first component can be a SAM component linked to a reactive group or recognition group, a spacer arm or a monovalent moiety. Subsequently, the second component is contacted with the substrate. This second component can either be added in stoichiometric equivalence, stoichiometric excess or can again be used to underlabel to leave sites open for yet a third component. It is also possible to displace some fraction of the first adsorbed species by a second species, thereby forming a mixture on the surface.

In certain preferred embodiments, the organic layer comprises:

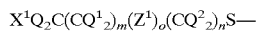

wherein, $X^1$ is a member selected from the group consisting of H, halogen and recognition moieties; Q, $Q^1$ and $Q^2$ are independent members selected from the group consisting of H and halogen; $Z^1$ is a member selected from the group consisting of —$CQ_2$—, —$CQ^1_2$—, —$CQ^2_2$—, —O—, —S—, —$NR^1$—, —$C(O)NR^1$ and $R^1NC(O)$—, in which; $R^1$ is a member selected from the group consisting of H, alkyl, substituted alkyl, aryl, substituted aryl, heteroaryl and heterocyclic groups; m is a number between 0 and 40; and n is a number between 0 and 40 and o is a number between 0 and 5.

In yet a further preferred embodiment, Q, $Q^1$ and $Q^2$ are independently members selected from the group consisting of H and fluorine. In a further preferred embodiment, $R^2$ is a member selected from H and $CH_3$. In yet another preferred embodiment u is a number between 5 and 20.

When the organic layer is formed from a halogenated organosulfur compound, the organic layer can comprise a single halogenated compound or more than one halogenated compound having different structures. Additionally, these layers can comprise both non-halogenated and halogenated organosulfur compounds.

In certain preferred embodiment of this aspect of the invention, the organosulfur layer comprises a member selected from the group consisting of —$S(CH_2)_nOH$, —$S(CH_2)_nCOOH$, —$S(CH_2)_nCH_3$, $HOCH_2CH_2(OCH_2CH_2)_mS$— and combinations thereof; m is an integer between 2 and 50; and n is an integer between 1 and 25. In a still further preferred embodiment, n is an integer between 5 and 15. In certain embodiments, the organic layer will include only these molecules, while in others one or more of these species will be mixed with one or more additional species.

Although, each of the components of the organic layer discussed herein are appropriate for practicing this aspect of the invention, in preferred embodiments, the organosulfur layer further comprises —$S(CH_2)_mX^1$, wherein $X^1$ is a recognition moiety; and m is an integer from 1 to 25. In another preferred embodiment, m is an integer from 5 to 15.

D.2 Hydrophilic Polymers

In a preferred embodiment, the organic layer includes a hydrophilic polymer. The hydrophilic polymer can optionally comprise an $X^1$. A number of hydrophilic polymers are useful in practicing the present invention. Both charged and uncharged polymers are of use, however, uncharged polymers are preferred. Suitable uncharged polymers include, but are not limited to, polyethylene glycol (PEG), poly (vinylalcohol), poly(propyleneglycol) (PPG)-PEG co-polymers PEG-PPG co-block polymers and similar polymers. In a preferred embodiment, these polymers are derivatized with at least one sulfur-containing moiety. PEG-thiols of various molecular weights are commercially available (Shearwater Polymers, Huntsville, Ala.). The choice of an appropriate polymer and its modification for a particular purpose will be apparent and readily accessible to those of skill in the art.

In a further preferred embodiment, $R^1$ is a poly (ethyleneglycol) moiety. Polyethylene glycol (PEG) use in biotechnology and biomedical applications continuing to expand and has been reviewed (Poly(ethylene glycol) Chemisrty: Biotechnical and Biomedical Applications, J. M. Harris, Ed., Plenum Press, New York, 1992). Modification of enzymes (Chiu et al., *J. Bioconjugate Chem.*, 4: 290–295 (1993)), RGD peptides (Braatz et al., *Bioconjugate Chem.*, 4: 262–267 (1993)), liposomes (Zalipsky, S. *Bioconjugate Chem.*, 4: 296–299 (1993)), and CD4-IgG glycoprotein (Chamow et al., *Bioconjugate Chem.*, 4: 133–140 (1993)) are some of the recent advances in the use of polyethylene glycol. The modification of toxicity, pharmacokinetics, biodistribution and other biofunctions are a number of the promising areas for the use of this simple polymer. Surfaces treated with PEG have been shown to resist protein deposition and have improved resistance to thrombogenicity when coated on blood contacting biomaterials (Merrill, "Poly(ethylene oxide) and Blood Contact: A Chronicle of One Laboratory," in Poly(ethylene glycol) Chemistry: Biotechnical and Biomedical Applications, Harris, Ed., Plenum Press, New York, (1992), pp. 199–220). Accordingly, application of PEG based coatings to multilayered porous materials would be very useful for chromatography, analytical and medical devices. In the present invention, hydrophilic polymers such as PEG can be used to engineer preselected pore sizes and characteristics by the judicious choice of the size of the PEG(s) chosen as constituents of the organic layer.

Poly(ethyleneglycol) is known to impart hydrophilicity and protein adsorption resistance and to reduce the immunogenicity and antigenicity of materials to which it is bound. See, for example, Abuchowski et al., Enzymes as Drugs, Holcenberg et al., Eds., John Wiley & Sons, N.Y., (1981), pp. 367–383. Many methods are available in the art for attaching poly(ethyleneglycol) moieties to other molecules. Generally, to effect covalent attachment of polyethylene glycol (PEG) to another molecule, for example, a protein, the hydroxyl end-groups of the polymer are first converted into reactive functional groups. This process is frequently referred to as "activation" and the product is called "activated PEG".

Many activated derivatives of poly(ethyleneglycol) are available commercially and in the literature. It is well within the abilities of one of skill to choose, and synthesize if necessary, an appropriate activated PEG derivative. At present, the most common form of activated PEG used for preparation of protein conjugates is poly(ethylene glycol) succinoyl-N-hydroxysuccinimide ester (SS-PEG). This derivative reacts quickly with proteins (30 min) under mild conditions yielding active yet extensively modified conjugates and, thus, is appropriate for use in practicing the present invention. See, Abuchowski et al. *Cancer Biochem. Biophys.*, 7: 175–186 (1984). In addition, many other activated PEG groups can be used in the present invention. Some of these are detailed below.

Activation of PEG has been reported to be accomplished by the use of reactive functional groups including cyanurylate (Abuchowski et al., *J. Biol. Chem.*, 252: 3582–3586 (1977); Jackson et al., *Anal. Biochem.*, 165: 114–127 (1987); Koide et al., *Biochem Biophys. Res. Commun.*, 111: 659–667 (1983)), tresylate (Nilsson et al., *Methods Enzymol.*, 104: 56–69 (1984); Delgado et al., *Biotechnol. Appl. Biochem.*, 12: 119–128 (1990)); N-hydroxysuccinimide derived active esters (Buckmann et al., *Makromol. Chem.*, 182: 1379–1384 (1981); Joppich et al., *Makromol. Chem.*, 180: 1381–1384 (1979); Abuchowski et al., *Cancer Biochem. Biophys.*, 7: 175–186 (1984); Katreet al. *Proc. Natl. Acad. Sci. U.S.A.*, 84: 1487–1491 (1987); Kitamura et al., *Cancer Res.*, 51: 4310–4315 (1991); Boccu et al., *Z. Naturforsch.*, 38C: 94–99 (1983), carbonates (Zalipsky et al., Poly(ethylene glycol) Chemistry: Biotechnical and Biomedical Applications, Harris, Ed., Plenum Press, New York, 1992, pp. 347–370; Zalipsky et al., *Biotechnol. Appl. Biochem.*, 15: 100–114 (1992); Veronese et al., *Appl. Biochem. Biotech.*, 11: 141–152 (1985)), imidazolyl formates (Beauchamp et al., *Anal. Biochem.*, 131: 25–33 (1983); Berger et al., *Blood*, 71: 1641–1647 (1988)), 4-dithiopyridines (Woghiren et al., *Bioconjugate Chem.*, 4: 314–318 (1993)), isocyanates (Byun et al., *ASAIO Journal*, M649-M-653 (1992)) and epoxides (U.S. Pat. No. 4,806, 595, issued to Noishiki et al., (1989). Other linking groups include the urethane linkage between amino groups and activated PEG. See, Veronese, et al., *Appl. Biochem. Biotechnol.*, 11: 141–152 (1985).

Various activated polyethylene glycols (PEG) have been effectively used in such fields as protein modification (Abuchowski & Davis, 1981, supra), peptide chemistry (Zalipsky, et al., *Int, J. Peptide Protein Res.*, 30: 740–783 (1987)) and preparation of conjugates with biologically active materials (Zalipsky, et al., *Eur. Polym. J.*, 19: 1177–1183 (1983) and Zalipsky et al., *Polymer Preprints, Am. Chem. Soc. Div. Polym. Chem.*, 27(1): 1–2 (1986)).

Also of use in the present invention are succinidyl carbonate activated PEGs, namely, poly(ethylene glycol)-succinidyl carbonate (SC-PEG). These materials react to yield attachment through stable urethane linkages. The reactivity of these agents, are comparable to the conventionally used SS-PEG. Thus, high degrees of modification are achievable in mild conditions (aqueous buffers, pH 5.8–11, preferably pH 7.0–9.5) within about 30–60 min. and moderate temperatures (4°–40° C). Additionally, the agents are soluble in a variety of organic solvents, thus being useful and important in the coupling of low molecular weight, partially protected peptides and other biologically useful ligands. See, U.S. Pat. No. 5,122,614, issued Jun. 16, 1992 to Zalipsky.

PEG useful in practicing the present invention does not have to be of a particular molecular weight, but it is preferred that the molecular weight be between 500 and 40,000; more preferably between 2,000 and 20,000.

In other preferred embodiments, the PEG does not have an $X^1$ group at a terminus and the organic layer comprises:

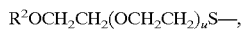

in which $R^2$ is a member selected from the group consisting of H, alkyl and acyl; and u is a number between 1 and 50.

E. Recognition Moieties

As used herein, the term "recognition moiety" refers to molecules which are attached to one or more organic layer components. The recognition moieties can interact with the analyte via either attractive or repulsive mechanisms. In one exemplary embodiment, the analyte and the recognition moiety form an intimately associated pair by, for example, covalent bonding, ionic bonding, ion pairing, van der Waals association and the like. In another exemplary embodiment, the analyte and recognition moiety interact by a repulsive mechanism such as incompatible steric characteristics, charge-charge repulsion, hydrophilic-hydrophobic interactions and the like.

Recognition moieties can be selected from a wide range of small organic molecules (e.g., drugs, pesticides, toxins, etc.), organic functional groups (e.g., amines, carbonyls, carboxylates, etc.), biomolecules, metals, metal chelates and organometallic compounds.

When the recognition moiety is an amine, in preferred embodiments, the recognition moiety will interact with a structure on the analyte that is complementary to (e.g., binding, complexing, ion-pairing) with the amine (e.g., carbonyl groups, alkylhalo groups). In another preferred embodiment, the amine is protonated by an acidic moiety on the analyte of interest (e.g., carboxylic acid, sulfonic acid). In still another preferred embodiment, the amine is quaternized and acts as an ion-exchange moiety.

In certain preferred embodiments, when the recognition moiety is a carboxylic, or other acid, the recognition moiety will interact with the analyte by, for example, complexation (e.g., metal ions) or ion-pairing (e.g., quaternary ammonium cations). In still other preferred embodiments, the carboxylic acid will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds that are being screened for their ability to interact with an analyte of choice. As such, drug moieties that are useful in practicing the instant invention include drugs from a broad range of drug classes having a variety of pharmacological activities.

Classes of useful agents include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine) ;diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g. imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, α-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or antithyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with antiinflammatory activity, such as sulindac, etodolac, ketoprofen and ketorolac, are also of use. Other drugs of use in conjunction with the present invention will be apparent to those of skill in the art.

The above enumerated, and other molecules, can be attached to the organic layer by methods well-known to those of skill in the art. Ample guidance can be found in literature devoted to, for example, the fields of bioconjugate chemistry and drug delivery. For example, one of skill, faced with a drug comprising an available amine will be able to choose from among a variety of amine derivatizing reactions, locate an appropriately functionalized partner (e.g., a carboxylic acid terminated thiol) for the organic layer and react the partners under conditions chosen to effect the desired coupling (e.g., dehydrating agents, e.g., dicyclohexylcarbodiimide). See, for example, Modification of Proteins: Food, Nutritional, and Pharmacological Aspects, Feeney et al., Eds., American Chemical Society, Washington, D.C., 1982, pp. 370–387; Polymeric Drugs and Drug Delivery Systems, Dunn et al., Eds., American Chemical Society, Washington, D.C., 1991.

When the recognition moiety is a chelating agent, crown ether or cyclodextrin, host-guest chemistry will dominate the interaction between the recognition moiety and the analyte. The use of host-guest chemistry allows a great degree of recognition-moiety-analyte specificity to be engineered into a device of the invention. The use of these compounds to bind to specific compounds is well known to those of skill in the art. See, for example, Pitt et al., "The Design of Chelating Agents for the Treatment of Iron Overload," In, Inorganic Chemistry in Biology and Medicine; Martell, Ed., American Chemical Society, Washington, D.C., 1980, pp. 279–312; Lindoy, The Chemistry of Macrocyclic Ligand Complexes; Cambridge University Press, Cambridge,1989; Dugas, Bioorganic Chemistry; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, Modification of Proteins: Food, Nutritional, and Pharmacological Aspects;" Feeney, et al., Eds., American Chemical Society, Washington, D.C., 1982, pp. 370–387; Kasina et al., *Bioconjugate Chem.*, 9: 108–117 (1998); Song et al., *Bioconjugate Chem.*, 8: 249–255 (1997).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity. See, for example, Szejtli, Cyclodextrins and Their Inclusion Complexes; Akademiai Klado, Budapest, 1982; and Bender et al., Cyclodextrin Chemistry Springer-Verlag, Berlin, 1978.

Cyclodextrins are able to form inclusion complexes with an array of organic molecules including, for example, drugs, pesticides, herbicides and agents of war. See, Tenjarla et al., *J. Pharm. Sci.*, 87: 425–429 (1998); Zughul et al., *Pharm. Dev. Technol.*, 3: 43–53 (1998); and Albers et al., *Crit. Rev. Ther. Drug Carrier Syst.*, 12: 311–337 (1995). Importantly, cyclodextrins are able to discriminate between enantiomers of compounds in their inclusion complexes. Thus, in one preferred embodiment, the invention provides for the detection of a particular enantiomer in a mixture of enantiomers. See, Koppenhoefer et al., *J. Chromatogr., A* 793: 153–164 (1998).

The cyclodextrin recognition moiety can be attached to a SAM component, through a spacer arm or directly to the metal. See, Yamamoto et al., *J. Phys. Chem. B,* 101: 6855–6860 (1997). Methods to attach cyclodextrins to other molecules are well known to those of skill in the chromatographic and pharmaceutical arts. See, Sreenivasan, K. J., *Appl. Polym. Sci.,* 60: 2245–2249 (1996).

In a presently preferred embodiment, the recognition moiety is a polyaminocarboxylate chelating agent such as ethylenediaminetetraacetic acid (EDTA) or diethylenetriaminepentaacetic acid (DTPA). These recognition moieties can be attached to any amine-terminated component of a SAM or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the $\epsilon$-amine groups of lysine residues. Furthermore, these molecules can be adsorbed onto the surface of the substrate or SAM by non-specific interactions (e.g., chemisorption, physisorption).

Recognition moieties which are antibodies can be used to recognize analytes which are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. No. 5,147,786, issued to Feng et al. on Sep. 15, 1992; U.S. Pat. No. 5,334,528, issued to Stanker et al. on Aug. 2, 1994; U.S. Pat. No. 5,686,237, issued to Al-Bayati, M. A. S. on Nov. 11, 1997; and U.S. Pat. No. 5,573,922, issued to Hoess et al. on Nov. 12, 1006. Methods for attaching antibodies to surfaces are also known in the art. See, Delamarche et al. *Langmuir*, 12: 1944–1946 (1996).

E.1 Reactive Groups

"Reactive groups," as used herein refers to a subset of recognition moieties. The members of this subset can be used to attach recognition moieties to SAM components or, alternatively, they can themselves serve as recognition moieties. For example, an amine-bearing SAM component can be used to bind a carboxylic acid-containing recognition moiety onto the SAM, or it can be used to "recognize" a carboxylic, or other acid, in a solution, vapor and the like. One principle of recognition using reactive groups can be broadly stated; materials having electron deficient (e.g., electrophilic) organic layers can be used to recognize electron rich (e.g., nucleophilic) species and vice-versa. Moreover, acids can be used to recognize bases and vice versa.

The reactive groups can also be used to tether recognition groups onto the materials of the invention either before or after the organic layer has been deposited onto the metal layer. In certain circumstances, it will be desirable to assemble a batch of the porous material having a reactive group on its surface. The material can be stored and aliquots can be used to bind recognition moieties as the materials are needed. Alternatively, each member of a set of porous substrates having the same organic layer can be reacted with a different recognition preparation of an array of differentially functionalized porous materials. This method is analogous to combinatorial library methods and it can be used to prepare an array of porous materials having different characteristics. These materials can then be screened in operation for desirable properties. Many other variations of and uses for this strategy will be readily apparent to those of skill in the art. The nature of useful reactive groups is discussed in greater detail below.

The reactive functional groups can be chosen such that they do not participate in, or interfere with, the reaction controlling the assembly of the various SAM components or the attachment of the functionalized SAM component onto the metal film. Alternatively, the reactive functional group can be protected from participating in the reaction by the presence of a protecting group. Those of skill in the art will understand how to protect a particular functional group from interfering with a chosen set of reaction conditions. For examples of useful protecting groups, see Greene et al., Protective Groups in Organic Synthesis, John Wiley & Sons, New York, 1991.

The discussion that follows focuses on the attachment of a reactive SAM component to the metal film. This focus is for convenience only and one of skill in the art will understand that the discussion is equally applicable to embodiments in which the SAM component-recognition moiety cassette is preformed prior to its attachment to the substrate. As used herein, "reactive SAM components" refers to components that have a functional group available for reaction with a recognition moiety or other species following the attachment of the component to the substrate.

Currently favored classes of reactions available with reactive SAM components are those which proceed under relatively mild conditions. These include, but are not limited to nucleophilic substitutions (e.g., reactions of amines and alcohols with acyl halides), electrophilic substitutions (e.g., enamine reactions) and additions to carbon-carbon and carbon-heteroatom multiple bonds (e.g., Michael reaction, Diels-Alder addition). These and other useful reactions are discussed in March, Advanced Organic Chemistry, Third Ed., John Wiley & Sons, New York, 1985.

According to the present invention, a membrane's surface can be functionalized with SAM components and other species by attaching a reactive SAM component to the metal film in such a way as to derivative the metal film with a plurality of available reactive functional groups. Reactive groups which can be used in practicing the present invention include, for example, amines, hydroxyl groups, carboxylic acids, carboxylic acid derivatives, alkenes, sulfhydryls, etc.

In a preferred embodiment, the reactive group is tethered to the metal surface by an agent displaying avidity for that surface. In a presently preferred embodiment, the substrate includes a silver film or a gold film and the group that reacts with the metal surface comprises a thiol, sulfide or disulfide such as:

wherein $R^1$ is a linking group between sulfur and $X^1$, and $X^1$ is a reactive group or a protected reactive group. $X^1$ can also be a recognition moiety as discussed below. Y is a member selected from the group consisting of H, $R^2$ and $R^2$—S—, wherein $R^1$ and $R^2$ are independently selected. When $R^1$ and $R^2$ are the same, symmetrical sulfides and disulfides result, and when they are different, asymmetrical sulfides and disulfides result.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding halo-amines, halo-carboxylic acids, etc. by reaction of these halo precursors with sodium sulfhydride. See, for example, Reid, Organic Chemistry of Bivalent Sulfur, vol. 1, pp. 21–29, 32–35, vol. 5, pp. 27–34, Chemical Publishing Co., New York, 1958, 1963. Additionally, functionalized sulfides can be prepared via alkylthio-de-halogenation with a mercaptan salt. See, Reid, Organic Chemistry of Bivalent Sulfur, vol. 2, pp. 16–21, 24–29, vol. 3, pp. 11–14, Chemical Publishing Co., New York, 1960. Other methods for producing compounds useful in practicing the present invention will be apparent to those of skill in the art.

Many reactive groups and protected reactive groups of use in the present invention will be apparent to those of skill in the art. One of skill will be able to ascertain and purchase or synthesize the reactive organic layer constituent needed for a particular purpose. Representative reactive functional groups ($X^1$) include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides:

(h) amine or sulfhydryl groups which can be, for example, acylated or alkylated;

(i) alkenes which can undergo, for example, cycloadditions, acylation, Michael addition, etc.; and (j) epoxides which can react with, for example, amines and hydroxyl compounds.

F. Conjugation

A recognition moiety can be conjugated to a component of an organic layer by any of a large number of art-known attachment methods. For example, in one preferred embodiment, a reactive SAM component is attached to the substrate and the recognition moiety is subsequently bound to the SAM component via the reactive group on the SAM component and a group of complementary reactivity on the recognition moiety. See, for example, Hegner et al., *Biophys. J.*, 70: 2052–2066 (1996). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a recognition moiety.

Peptides and nucleic acids can be attached to a SAM component. Both naturally-derived and synthetic peptides and nucleic acids are of use in conjunction with the present invention. These molecules can be attached to a SAM component by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al., *Nucleic Acids Res.*, 24: 3031–3039 (1996).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art. See, for example, "Special Methods in Peptide Synthesis," In, The Peptides: Analysis, Synthesis, Biology, Vol. 2: Gross, et al., Eds., Academic Press, New York (1980). Many useful monomers are commercially available (Bachem, Sigma, etc.). This masked group can then be unmasked following the synthesis, at which time it becomes available for reaction with a SAM component or a spacer arm.

In other preferred embodiments, the peptide is attached directly to the metal film. See, Frey et al. *Anal. Chem.,* 68: 3187–3193 (1996). In a particularly preferred embodiment, the peptide is attached to a silver or a gold film through a sulfhydryl group on a cysteine residue. In another preferred embodiment, the peptide is attached through a thiol to a spacer arm which terminates in, for example, an iodoacetamide, chloroacetamide, benzyl iodide, benzyl bromide, alkyl iodide or alkyl bromide. Similar immobilization techniques are known to those of skill in the art. See, for example, Zull et al., *J. Ind. Microbiol.,* 13: 137–143 (1994).

G. Spacer Arms

As used herein, the term "spacer arm," refers to constituents of the organic layer that have a different structure than the bulk of the organic layer and which bear either reactive groups, recognition moieties or combinations thereof.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the reactive group and/or recognition moiety can be controlled. Properties that are usefully controlled include, for example, hydrophobicity, hydrophilicity, surface-activity and the distance of the reactive group and/or recognition moiety from the surface of the substrate and/or the SAM. For example, in a SAM composed of alkanethiols, the recognition moiety can be attached to the metal film or a SAM component via an amine terminated poly (ethyleneglycol). Numerous other combinations of spacer arms and SAMs will be apparent, and are accessible, to those of skill in the art.

In addition to the use of hydrophilic polymers, the hydrophilicity of the organic layer can be enhanced by reaction with polar molecules such as amine-, hydroxyl- and polyhydroxyl-containing molecules. Similar strategies can be used to increase hydrophobicity (e.g, use of long-chain fatty acid derivatives) and to enhance the surface activity of the material (e.g., use of detergents, surfactants).

In another embodiment, the spacer serves to distance the reactive group and/or recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

H. Changes of State

The membranes of the present invention can be assembled such that the organic layer comprises a switchable group that undergoes a change of state upon being contacted by some external agent or force. The switchable group can be the recognition moiety, a portion of the recognition moiety and/or the group to which the recognition moiety is attached. The change in state can be, for example, an alteration in the conformation, electronic configuration, charge, polarity, dipole moment or steric bulk of the group. The change in the state of the group can be utilized to affect the membrane properties and to assemble membranes that are switchable between at least two different states.

The change in state can be brought about by a range of external conditions or forces including, for example, changes in fluid pH, ionic strength and/or redox potential. Additionally, changes in state can be brought about by exposing the switchable group to forces such as light, heat, magnetic and electrical fields.

In a preferred embodiment, the change of state is utilized to alter the availability of a recognition moiety to its binding partner. For example, in a first state, the switchable group can present a recognition moiety in a binding mode. When switched into its second state, the binding moiety becomes unavailable for binding or it binds with less affinity. Thus, by switching between the two states an analyte can be, for example bound to and then expelled from the membrane. Alternatively, the recognition moiety can be maintained in its non-binding conformation until a desired time when the change of state is initiated and the membrane binds the analyte.

In another preferred embodiment, the switchable group can be used to vary the size or the charge of the pores. Thus, the permselectivity of a membrane can be varied between at least two states utilizing the available states of the switchable group. For example, a group that is switched by a change in pH might exist in both an acidic and a basic form. In one example, the acidic form will be charged (e.g., amine to ammonium cation). In its neutral form, the membrane will allow positively charged analytes of the proper size to pass through the membrane. If the membrane is protonated, however, the positively charged species will be repelled by the similar charges on the membrane.

In those embodiments wherein the passage of a species through the membrane is influenced by the size of the species, the size of the pores can be switched between a first and a second state. In this embodiment, one of the states will be characterized by a greater steric bulk of the switchable group.

Switchable groups appropriate for use in conjunction with the present invention include, for example, azobenzene derivatives. Azobenzenes exist in one of two switchable isomers, the "trans" and the "cis" isomers. See, for example, Yu et al., *Langmuir* 12: 2843–2848 (1996); Kumano et al., *Polymer J.* 16(6): 461–470 (1984); Seki et al., *Langmuir* 9: 211–217 (1993); and Sekkat et al., *Langmuir* 11: 2855–2859 (1995). Other useful groups include, for example, spiropyrans and related compounds and redox couples such as ferrocene (Chidsey, *Science* 251: 919 (1991)), viologen (DeLong et al., *Langmuir* 6: 709 (1992)), and ruthenium polypyridyl complexes (Finkles et al., *J. Am. Chem. Soc.* 114: 3173 (1992)). Other useful switchable groups will be apparent to those of skill in the art.

The switchable membranes are of use in each of the aspects and embodiments of the invention discussed below.

I. Methods

In addition to the novel materials detailed above, the present invention also includes methods for using and manufacturing these materials. The methods include purification strategies (e.g., ion exchange, dialysis) and assays.

I.1. Ion Exchange

Ion-exchange is an ubiquitous technique in which cations or anions in a fluid are either removed from, or concentrated by the ion exchange membrane. Although, many different types of ion exchange membranes are known in the art, they are generally based on an organic polymer structure. For example, in U.S. Pat. No. 3,884,885, a fluorinated polymer containing pendent, ion-exchange groups in the form of —$SO_3H$ or —$SO_2NH_2$ is disclosed. Further, preparation of fluorocarbon cation-exchange polymer membranes by reaction of a cation-exchange membrane carrying as its ion-exchange radical a sulfonic acid radical with primary to tertiary monoamines or, alternatively, with quaternary ammonium salts is disclosed in U.S. Pat. No. 4,246,091. Additionally, many ion-exchange membranes are commercially available (e.g., Bio-Rad Laboratories, Richmond, Calif.).

Ion-exchange membranes have been put to a number of uses on both laboratory and industrial scales. For example separation of organic liquids utilizing an ion-exchange membrane is disclosed by Pasternak et al. in U.S. Pat. Nos. 4,798,674; 4,877,529; 4,952,318; and in U.S. Pat. No. 5,006,576. Additionally, ion-exchange devices have been used in water treatment, food processing, pharmaceutical manufacturing, chemical purification, hydrometallurgy, metal processing, waste treatment, gas absorption and as catalysts.

In spite of their useful properties, the straight-forward assembly of membranes specific for certain ions or classes of ions or having certain desirable properties remains a somewhat elusive goal. Two approaches for assembling ion-exchange membranes are prevalent in the art; the polymerization of monomers bearing ion-exchange moieties and the modification of polymeric membranes with ion-exchange moieties. Both of these methods are limited in the identities of ion-exchange moieties that can be incorporated into the membranes and in the morphology of the membranes produced.

The materials of the present invention can be tailored for a particular ion-exchange application by a straight-forward attachment of a selected recognition moiety to the organic layer of the membranes of the invention.

Thus, in a fourth aspect, the present invention provides a method for removing an ion from a fluid, said method comprising:

(a) contacting said fluid with an ion exchange medium comprising:
   (i) a porous substrate;
   (ii) a metal film adhered onto said substrate; and
   (iii) an organic layer attached to said metal film, said organic layer comprising a recognition moiety that interacts with said ion.

The interaction between the recognition moiety and the ion can be either attractive or repulsive. In those embodiments, wherein the interaction is attractive, the ion can be bound to the ion-exchange membrane and physically removed from the solution by removing the membrane from the solution. In a preferred embodiment, the method further comprises passing the ion through the ion exchange medium. In yet another preferred embodiment, the interaction is repulsive and the ion cannot pass through or bind to the membrane.

The recognition moiety can comprise any group having ion-exchange capabilities, however, in a preferred embodiment, the recognition moiety is a member selected from the group of amines, quaternary amines, heterocyclic amines, sulfonamides, quaternary phosphonium, tertiary sulfonium, acids, chelating agents, crown ethers, cyclodextrins and combinations thereof.

The method of the invention can be used to separate a single ion or more than one ion from other species in a mixture. As with conventional ion exchange methods, the present method can be used to separate ions having dissimilar charges. Additionally, in a preferred embodiment, the method of the invention can be used to separate selectively two ions having identical charges. Ions with identical charges can be separated by, for example, controlling the size of the pores such that a smaller ion is preferentially transported across the membrane.

The materials of the invention can be used for methods in which the separation is achieved by passive diffusion across the membrane. Such processes are referred to as "diffusion dialysis" processes. Diffusion dialysis is a simple ion exchange membrane process that separates ionic, non-ionic or colloidal species from an aqueous acid, base, or salt solution based on differences in diffusion rates. This method utilizes a concentration difference across the membrane as the driving force. Examples include acid dialysis and base dialysis.

Acid diffusion dialysis can be used for a range of purposes, including purification and/or analysis of organic and inorganic molecules, recovery of acids such as HCl, $HNO_3$, HF and $H_2SO_4$ from spent pickling baths, recovery of acids from metal finishing baths, recovery of mineral acids from battery waste and recovery of hydrochloric acid from uranium processing. Base diffusion dialysis can be used, inter alia, for the purification and/or analysis of organic and inorganic materials, in the recovery of caustic and aluminum from aluminum chemical milling, anodizing, aluminum surface finishing baths, recovery of caustic from, for example, photographic baths and electronic component processing (Aqualytics, Inc.).

A typical diffusion dialysis apparatus comprises at least one permselective diffusion membrane (either cationic or anionic). The membrane divides a dialysis vessel into two or more compartments. The feed fluid is on one side of the membrane at the beginning of the process. Typically, a free acid or base will diffuse across the membrane into the product compartment of the vessel. Alternatively, one of these components can be repelled by the membrane and concentrated in the feed fluid.

In addition, to methods in which the ion-exchange or other separation is effected by passive diffusion, he membranes of the present invention, due to the conductive metallic layer can be used in processes such as electrodialysis. Electrodialysis is an electrically driven separation modality utilizing an ion exchange membrane. This technique is capable of separating, concentrating and purifying selected ions from aqueous mixtures. Electrodialysis is similar to evaporation or reverse osmosis. It can be used, for example, to recover pure water from a salt solution or concentrate the total dissolved solids in a waste stream.

Electrodialysis utilizes a system in which ions migrate through the membrane from a less concentrated to a more concentrated solution as a result of the ions' respective attractions to a positive electrode (anode) and a negative electrode (cathode), created by direct electric current. Application of a current causes cations to migrate toward the cathode, and anions to migrate toward the anode. Upon contacting an ion exchange membrane surface, the membrane properties (i.e., charge and pore size) determine whether the ion is repelled or allowed to pass through it.

Electrodialysis has been used for a number of applications including, desalting and purification of organic acids and solvents including glycol and amines, desalting of foods such as whey, soy sauce, vinegar, hydrolyzed vegetable protein, sugars and wine, deacidification of foods, concentration of dilute acid, base and salt streams, recovery of salts, acids, or alkali from industrial rinse waters, mineral acid separation, phosphoric acid recovery, drinking water nitrate reduction, synthesis of organic and amino acids, waste water minimization, potable water production from brackish water.

I.2. Affinity-Based Membrane Separations

Affinity-based purification methods, such as affinity chromatography enable the efficient isolation of species such as biological molecules or biopolymers by utilizing their recognition sites for certain supported chemical/biological structures with a high degree of selectivity. Previous affinity-based methods have been predominantly chromatographic, utilizing materials of varying chemical structure as supports. For example, agarose gels and cross-linked agarose gels have been the most widely used support materials. Although their hydrophilicity makes them relatively free of nonspecific binding, their compressibility makes them less attractive as carriers in large scale processing, such as in manufacturing. Controlled-pore glass (CPG) beads have also been used in affinity chromatography. Although high throughputs can be obtained with columns packed with CPG, this carrier is even more expensive than agarose beads. Cellulose particles have also been used by immunochemists for synthetic affinity sorbents. However, compared to agarose gels, cellulose particles are formed with more difficulty and therefore, have received less attention in the preparation of affinity sorbents for enzymes.

A review of current affinity chromatographic matrices, leads to the conclusion that there exists a need for materials and method useful both for ion exchange and affinity-based purifications which will have high stability, high porosity, low non-specific adsorption, high through-put, non-compressibility, and which will be useful for both laboratory and industrial-scale biological separations. It is at the industrial level of manufacturing, especially, where the aforementioned drawbacks of the prior art have had their most important effect and where this need is the strongest.

Large-scale membrane-mediated purifications are well-known in processes, such as the purification of organic chemicals, pharmaceuticals, waste-water and gas separations. Thus, a membrane-based affinity separation material and method is an attractive alternative for chromatographic processes.

The affinity of a membrane-bound recognition moiety for an analyte can be exploited to purify that analyte. In this embodiment of the present invention, the materials of the invention are broadly analogous to affinity chromatography matrices. The methods are similarly analogous to affinity chromatographic methods. Although the materials of the invention can be used in a range of affinity purification protocols, two methodologies are currently preferred. In the first of these, the porous material is incubated with a fluid containing the analyte. Following the period of incubation, the membrane is removed from the fluid and the analyte is freed from the membrane. In a second embodiment, the organic layer comprises a recognition moiety that, because of its affinity for the analyte, facilitates the transport of the analyte across the membrane.

Thus, in a fifth aspect, the present invention provides a method for isolating a molecule from other molecules by affinity dialysis comprising:

(a) contacting the molecule with a multilayered porous material comprising:
    a porous substrate;
    a metal film adhered onto the substrate; and
    an organic layer attached to the metal film, the organic layer comprising a recognition moiety (c) forming a complex between the recognition moiety.

In a preferred embodiment, after the membrane and a fluid containing the molecule are contacted and incubated together, the membrane is removed from the fluid and the method further comprises;

(d) washing the membrane-molecule complexes with a solvent for the other molecules.

Following the purification, it will often be desirable to remove the purified molecule from the membrane. Thus, in a preferred embodiment, the method of the invention further comprises disrupting the complex between the recognition moiety and the molecule, thereby separating the molecule from the membrane.

In another preferred embodiment, the molecule undergoing affinity separation interacts with the recognition moiety and is transported across the membrane at a rate higher than that at which other molecules in the fluid are transported. In this embodiment, the method further comprises;

(d) disrupting the membrane-molecule complexes, thereby passing the molecule through the membrane.

The membrane-molecule complex can of a transient nature and easily disrupted by normal kinetic/thermodynamic processes (e.g., low binding affinity, concentration gradients, diffusion, etc.). Alternatively, the complex can be disrupted by a change in the fluid conditions (e.g., ionic strength, pH, temperature, etc.). In general, the formation of the complex will facilitate the transport of the analyte across the membrane.

The concept of facilitated transport across membranes is recognized in the art. See, for example, Lakshmi et al., *Nature* 388(21), 758–760 (1997); Noble, *Chem. Eng. Progr.* 85: 58–70 (1989); Noble et al., *J. Membr. Sci.* 75: 121–129 (1992). Briefly, the concept of facilitated transport involves the conjugation to a membrane of a species selective for an analyte. The membrane-conjugated species recognizes the analyte and binds to or otherwise forms a complex with the analyte. Thus, the present invention provides materials and methods for achieving the affinity purification of species through a facilitated transport mechanism.

Although it is within the scope of the present invention to utilize membrane-based affinity separation methods for the purification of any member of any class of molecules, in a preferred embodiment, the molecule being purified is a biomolecule. In further preferred embodiments, the biomolecule is a member selected from the group consisting of peptides, enzymes, enzyme substrates, carbohydrates, nucleic acids, antibodies, antigens and combinations thereof.

The choice of appropriate recognition groups for performing a particular affinity chromatographic separation will be apparent to those of skill in the art, however, in preferred embodiments, the recognition moiety is a member selected from the group consisting of biomolecules, organic groups, metal chelates, organometallic moieties and combinations thereof. In preferred embodiments, the recognition moiety does not react with the analyte to convert it to another species. Thus, recognition moieties, such as apoenzymes, receptors and antibodies are currently preferred.

The literature is replete with articles, monographs, and books on the subject of affinity chromatography, including such topics as affinity chromatography supports, crosslinking members, ligands and their preparation and use. A sampling of those references includes, "Affinity chromatography: general methods," *Methods Enzymol.*, 182: 357–71 (1990); "Novel affinity-based processes for protein purification," *Ferment, Bioeng.*, 70(3): 199–209 (1990). "Applications of preparative high-performance liquid chromatography to the separation and purification of peptides and proteins," *J. Chromatogr.*, 492: 431–69 (1989); "Purification of enzymes by heparin-Sepharose affinity chromatography," *J. Chromatogr.*, 184(3): 335–45 (1980), "Principles of multi-enzyme purification by affinity chromatography," *Enzyme Eng.*, 4: 441–2 (1978); "General ligand affinity chromatography in enzyme purification; Ligands, affinity chromatography, enzyme purification," *J. Macromol. Sci., Chem.*, A10(1–2): 15–52 (1976); "Affinity purification of enzymes," *Chem. Technol.*, 5(9): 564–71 (1975); "Bioaffinity chromatography," *Pract. High Perform. Liq. Chromatogr.*, 193–206 (1976); "Affinity chromatography of plasma proteins-an overview," *Proc. Int., Workshop Technol. Protein Sep. Improv. Blood Plasma Fractionation*, 422–35; (1977) "Affinity chromatography of enzymes," *Affinity Chromatogr., Proc. Int. Symp.* 25–38, (1977) (Pub. 1978); "Protein immobilization and affinity chromatography," *Biotechnol. Appl. Proteins Enzymes. Pap. Conf.*, 83–102 (1976) (Pub. 1977); "Use of affinity chromatography in protein structure studies," *Pept., Proc. Eur. Pept. Symp.*, 11th, 203–22 (1971) (Pub. 1973); "Affinity chromatography of enzymes," *Fed. Eur. Biochem. Soc. Meet.*, [Proc] 30 (1974); and Affinity Chromatography: A Practival Approach, IRL Press Limited, Oxford England (1985). It is within the abilities of those of skill in the art to modify methods appropriate for preparing and utilizing affinity chromatographic media such that they can be used in conjunction with the porous materials of the invention.

To better illustrate this aspect of the invention, the following discussion, focusing on enzyme purification, is offered. The use of enzyme purification is intended to be illustrative and not limiting.

The starting point for designing an affinity matrix for removal of specific enzymes is to examine the structure of the enzyme and, particularly, the structure of the inhibitors of the enzymes. The complex formed between an enzyme and its inhibitor provides the best picture of how the enzyme may interact with the specific protein structure. Enzyme inhibition is always competitive and reversible as expressed by the following equation:

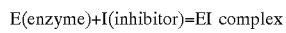

$$E(\text{enzyme}) + I(\text{inhibitor}) = EI \text{ complex}$$

In affinity dialysis, this reaction between enzyme and the membrane-bound inhibitor or substrate is used to selectively extract the enzyme from crude solutions, either as a batch or continuous process. In preferred embodiments, after washing away the contaminating proteins, the enzyme is freed from the membrane by introducing free ligand, which competes with the membrane for binding of the enzyme. The enzyme is then freed of inhibitor by dialysis or ultrafiltration techniques, or in the case of potent inhibitors by chemical processes that interfere with binding to the inhibitor.

The dialysis feed solution can contain a buffer solution which is preferably at neutral pH. Any nonreactive compound with a pKa near neutrality is satisfactory. Quite often a buffer such as N-[2-hydroxyethyl]piperazineN'-[2-ethanesulfonic acid] (HEPES) proves to be satisfactory. Other components can be included in the buffer, such as sucrose, 3-[3-cholamidopropyl)dimethylammonio]-1-propanesulfonate (CHAPS) to slow the rate of dissociation of enzyme having multiple subunits to inactive monomers. Other useful buffer solutions and additives for a given purpose will be apparent to those of skill in the art.

The flow rate through the membrane can vary over a wide range. An important consideration in the choice of flow rates is the rate constant for association and dissociation of the inhibitor and the enzyme. When the rates of association are slower than normal, slow flow rates are generally used.

Methods of controlling the flow include manipulating the concentration gradient of the enzyme and varying the pore size of the membrane.

Following its immobilization on the membrane, the bound enzyme is generally washed with buffer, or continuously dialyzed against fresh buffer, to remove the last traces of contaminating proteins.

After washing, the enzyme is removed from the membrane by including the free ligand, or another inhibitor or substrate for the enzyme in the wash buffer. Again, the rate constants for equilibration with particular inhibitors require special consideration. The half-life for dissociation of the inhibitor or substrate can be used as a guide for ascertaining appropriate flow rates or incubation times. If the rates are too slow to use continuous flow to remove the enzyme, removal is accomplished in a batch process, in which the membrane is flooded with free ligand and then incubated for a period (e.g., overnight) to allow the exchange to reach equilibrium.

Lastly, purified enzyme must be separated from the E-I complex. At this point, the purified enzyme is complexed with the eluting ligand. Removal of the ligand and reactivation of the enzyme is classically accomplished by dialysis or diafiltration. Similar methods are available for purification of other biomolecules.

In a variation on this method, the enzymes, or their apoenzyme analogues, can be utilized as components of the affinity membrane to isolate the components to which they bind.

Of particular interest is the immobilization of enzymes such as hydrolases, isomerases, proteases, amylases, and the like. These immobilized enzymes can then be used in biochemical reactors, as is otherwise well known in the art. In a preferred embodiment, the starting material does not pass through the membrane, however, the product will pass through the membrane and into a collection vessel on the other side of the membrane.

Antibodies can be similarly isolated by the use of a membrane having bound thereto one or more species recognized by the antibody. Alternatively, antibodies can be used in an affinity membrane to isolate the targets (e.g. antigen, receptor or receptor subunits) to which they bind. Briefly, in one embodiment, affinity dialysis involves immobilizing (e.g. on the porous material of the invention) one or more species of antibodies. A fluid containing the molecules (e.g., small molecular drugs, peptides, peptide mimetics, nucleic acids, etc.), cells, cellular lysate, or cellular homogenate are then contacted with the immobilized antibody which then binds to its cognate ligand. The remaining material is then washed away and the bound/isolated cognate ligand can then be released from the antibody for farther use. Adaptations of art-recognized methods for performing affinity chromatography are well within the abilities of those of skill in the art (see, e.g., U.S. Pat. Nos. 5,710,254; 5,491,096; 5,278,061; 5,110,907; 4,985,144; 4,385,991; 3,983,001, etc.).

It is now known that for the coupling of a biomolecule or a ligand to a solid matrix to present the coupled species with maximum affinity for its binding partner it is important that the ligand or biomolecule retain its active conformation after coupling to the matrix. For example, antibody molecules exist in their active forms only in a small number of conformations. The functional affinities vary widely upon coupling to a solid surface. Thus, the noncovalent interactions between the membrane and ligand with forces such as hydrogen bonding and hydrophobic interactions have manifest influence on antibody conformations. Since antibodies are bulky in structure, the physical character of the membrane, such as surface area and pore distribution, also is a consideration from a steric hindrance point of view. For example, it has been found that above the level of about 3–4 mg/gm of IgG bound to Sepharose™, additional bound IgG is ineffective as a ligand. Apparently, as higher levels of IgG are coupled to the Sepharose™, antibody activity actually diminishes due to crowding of IgG, preventing the action of the antibody. As a solution to this problem, the present invention provides a material in which the concentration and spacing of the bound antibody, or other molecule, can be rationally controlled and varied to optimize the separation parameters.

Typical ligands of use in this aspect of the invention include, but are not limited to, DNA blood type antigen, anti-alpha feto protein, C1Q, protein A, protein G, polylysine, mucopolysaccharides such as heparin, methylated albumin, tryptophan, phenylalanine, concavaline A, and the like. For removal of proteolytic enzymes from IgG, episilonaminoacrylic acid, lysine, methyl-p-aminocyclohexane carboxylic acid, and trasylol, potential inhibitors, are preferred. For removal of mucopolysaccharides such as heparin, low molecular weight basic proteins (protamines) such as protamine sulfate are preferred. For removal of kallikrein and PKA, benzamidine is effective. For removal of endotoxins, polymyxin-B-sulfate is preferred.

As will be recognized by one skilled in the art, ligands suitable for the practice of the present invention include all ligands which may be immobilized by the affinity membrane and still maintain biological activity, such ligands being represented by, but not limited to, the following general classes amino acids; avidin-biotins; carbohydrates; glutathiones; hydrophobic matrices; immunoglobulins; insoluble proteins; lectins; nucleotides; polyamino and polynucleic acids; and specialty ligands.

Typical amino acids suitable as affinity ligands include L-alanine, L-arginine, L-asparagine, L-aspartic acid, L-cysteine, L-cystine, L-glutamic acid, L-glutamine, glycine, L-histidine, L-isoleucine, L-lysine, L-methionine, L-phenylalanine, L-proline, L-serine, L-threonine, L-thyroxine, D-tryptophan, L-tryptophan, L-tyrosine and L-valine.

Typical avidin-biotin ligands include avidin, biotin, desthiobiotin, diaminobiotin, and 2-iminobiotin.

Typical carbohydrates include the glucosamines, the glycopryranoses, the lactosamines, the fucosamines, the fucopyranosylamines, the galactosylamines, the glycopyranosides, and the like.

Typical glutathione ligands include glutathione, hexylglutathione, and sulfobromophthalein-S-glutathione.

Typical hydrophobic matrices include amino allyl, butyl, decyl, dodecyl, ethyl, hexyl, methyl, octyl, pentyl, phenyl and propyl.

Typical immunoglobulins include the IgG's, including anti-goat IgG, anti-human IgG, anti-mouse IgG, anti-rabbit IgG, goat IgG, human IgG, rabbit IgG, and anti-glucose-6-phosphate dehydrogenase.

Typical proteins include factor VIII von Willebrand factor complex (VIII:C/VII:RP complex); factor VIII procoagulant activity protein (VIII:C); von Willebrand factor (VIII:RP) (see, U.S. Pat. No. Re. 32,011); factor IX; vitamin K dependent clotting factors such as X, VII, II, protein C, and protein S; antithrombin III; tissue factor inhibitor; plasminogen activator inhibitor; tissue plasminogen activator; erythropoietin; colony stimulating factors; growth factors; protein C inhibitor; interleukins; labeled proteins; DNA probes; interferons; hepatitis vaccine; lipocordons; or any protein, peptide, or fragment to which a monoclonal antibody can be made or bound. The source of proteins such as VIII:C, VIII:RP and factor IX may be plasma or a recombinant source.

Typical insoluble proteins include aprotinin, fetuin, gelatin, globin, glycophorin, hemoglobin, insulin, lactalbumin, parvalbumin, protamine, protein-A, protein-G, ribose-binding protein, and trypsin inhibitor.

Typical lactins, include *Arachis hypogaea,* concanavalin A, *Dolichos biflorus,* glycine max, *Lens culinaris, Phytolacca americana, Pisum sativum,* and the like.

Typical nucleotides include the adenosine mono- and diphosphates, the cytidine di- and triphosphates, flavin mononucleotide, the guanosine mono-, di-, and triphosphates, and the uridine mono-, di-, and triphosphates.

Typical polyamino and polynucleic acids include DNA, polyadenylic acid, polycytidylic acid, polylysine, polyriboadinylic, polyribocytidylic, polyriboguanylic, polyriboinosinic acid, and polyuridylic.

In those embodiments in which the affinity membranes of the invention are configured within a device, a membrane of the invention will generally divide the device into two or more vessels appropriate for holding a fluid. Many materials that can be isolated using conventional affinity chromatography support materials can be isolated using the method of the present invention.

I.3. Size Exclusion Dialysis

In a sixth aspect, the invention provides a method of isolating a first molecule from a second molecule by size exclusion dialysis, comprising:
 (a) contacting the first and second molecule with a multilayered porous material comprising;
  a porous substrate;
  a metal film layered onto the substrate;
  a hydrophilic polymer attached to the metal film; and
 (b) passing the first molecule through the porous material while the second molecule is substantially retained thereby.

Any hydrophilic polymer known in the art can be used in this aspect of the invention. The hydrophilic polymers can be either charged or neutral compounds. In a presently preferred embodiment of this aspect of the invention, the hydrophilic polymer comprises poly(ethyleneglycol).

Size exclusion dialysis is a well-known methodology for separating molecules on the basis of differences in molecular size and/or weight. This form of dialysis is generally non-interactive, The membrane consists essentially of a porous network in which solute molecules are either retained by or passed through based on their hydrodynamic volumes; that is their size and shape. See, for example, Yau et al., Modern Size Exclusion Chromatography, Wiley-Interscience, New York, 1979.

As a sample passes through the size dialysis membrane, the solute molecules below the molecular weight cut-off are passed through the membrane by the pores in the membrane. Large molecules that cannot enter the pores do not pass through the membrane.

In this aspect of the invention, the porous network is formed from hydrophilic polymers. The pore size and the density of the network on the membrane material can be adjusted by varying the size and the amount of the hydrophilic polymer bound to the surface. Because organosulfur monolayers on metal surfaces typically form without an "islanding" effect when more than one compound is used, an array of homogeneous matrices with novel structures and useful properties can be formed by mixing varying concentrations of, for example, thiol-PEGs of different lengths (i.e., molecular weights). Further, a polymer mixture including hydrophilic polymers of different structure and/or different molecular weights can be used to vary the characteristics of the matrix. The choice of appropriate membrane characteristics will be apparent, and easily accessible, to one of skill in the art.

I.4. Assays

Assays based on specific binding reactions have been used for detecting a wide variety of components such as drugs, hormones, enzymes, proteins, antibodies, and infectious agents in various biological fluids and tissue samples. In general, the assays consist of an analyte, a binding substance for the analyte, and a means of detection such as a detectable label. Immunological assays involve reactions between immunoglobulins (antibodies) which are capable of binding with specific antigenic determinants of various compounds and materials (antigens). Other types of reactions include binding between avidin and biotin, protein A and immunoglobulins, lectins and sugar moieties and the like. See, for example, U.S. Pat. No. 4,313,734, issued to Leuvering; U.S. Pat. No. 4,435,504, issued to Zuk; U.S. Pat. Nos. 4,452,901 and 4,960,691, issued to Gordon; and U.S. Pat. No. 3,893,808, issued to Campbell.

These assay techniques provide the ability to detect both the presence and amount of small quantities of analytes and are useful in, for example medical diagnostics and forensic applications.

Thus, in an seventh aspect, the present invention provides a method for determining the presence or amount of an analyte in a test sample comprising:
 (a) contacting the test sample with a multilayered porous material comprising;
  a porous substrate;
  a metal film layered onto the substrate,
  an organic layer adhered to the metal film, the organic layer comprising a recognition moiety;
 (b) forming a complex between the recognition moiety and the analyte; and
 (c) detecting the analyte.

Assays of any format can be used in conjunction with the present invention. In an exemplary embodiment, the porous material of the invention is used as an assay substrate on which the assay is performed. Assay formats appropriate to this embodiment include sandwich assays, agglutination assays, competitive assays and immunoassays. Alternatively, the material of the invention can be used to distinguish between the analyte and another substance. For example, if the analyte is contaminated with an interfering substance, the material of the invention can facilitate the assay by excluding the interfering substance from the detection step.

In yet another embodiment, the analyte is bound to the membrane. The analyte is subsequently released from the membrane on contacting a binding partner having greater avidity for the analyte than that of the membrane.

In another exemplary embodiment, the material of the invention selectively transports the analyte across the membrane and into the apparatus utilized for detection. For example, if the analyte is negatively charged and the interfering is positively charged, a material having a positively charged recognition moiety will facilitate the transport of the analyte across the membrane.

When the membrane is used to transport or exclude a species, a presently preferred assay format is equilibrium dialysis. Equilibrium dialysis provides a method to determine ligand binding and association constants from measured and plotted ligand binding data. In a typical experimental apparatus, a porous material of the invention divides a vessel into two chambers. The functionality of the porous material will determine those molecules that will pass through the membrane and those that will be retained by the membrane. In a preferred embodiment, the membrane will allow a ligand to pass through the membrane, but will retain the ligand-binding partner (e.g., antibody, enzyme, etc.). In a typical equilibrium dialysis experiment utilizing an antibody, the same concentration of antibody is placed into one compartment of several dialysis vessels. Differing concentrations of ligands are placed in the other compartment and the system is allowed to come to equilibrium.

After the system has come to equilibrium, there will be an equal amount of free ligand in each compartment of the vessel. If the antibody binds the ligand, there will also be a population of bound ligand in the antibody-containing compartment. This will afford a correspondingly higher concentration of ligand in the antibody-containing compartment relative to the ligand only compartment. Therefore, by determining the total ligand each side of the container, the free ligand concentration can be determined and, by subtraction the concentration of the bound ligand can be determined. By constructing a bound/free versus bound plot, the $K_a$ for the can be determined. Additionally, by dividing the ligand bound at saturation by the total concentration of antibody used, the number of ligand binding sites on the antibody can be determined.

The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

Many other analysis formats can be utilized with the materials of the invention. The choice of assay format and the appropriate material and detection means to carry out the assay will be apparent to those of skill in the art.

Competition binding data can be analyzed by a number of techniques, including nonlinear least-squares curve fitting procedure. When the ligand is an antagonist for the receptor, this method provides the IC50 of the antagonist (concentration of the antagonist which inhibits specific binding of the ligand by 50% at equilibrium). The IC50 is related to the equilibrium dissociation constant (Ki) of the antagonist based on the Cheng and Prusoff equation: Ki=IC50/(1+L/Kd), where L is the concentration of the ligand used in the competitive binding assay, and Kd is the dissociation constant of the ligand as determined by Scatchard analysis. These assays are described, among other places, in Maddox et al., *J. Exp Med.*, 158: 1211 (1983); Hampton et al., Serological Methods, A Laboratory Manual APS Press, St. Paul, Minn., 1990. Other assay formats utilizing the material of the invention will be apparent to those of skill in the art.

Methods of detecting can utilize any art-recognized method of detecting the presence of a compound or a binding interaction including, but not limited to, optical, non-optical, coulometeric, potentiometric, fluorescent, chromophoric, luminescent and the like.

Exemplary optical detection means include interference enhanced reflection (IER) and surface plasmon resonance (SPR). In case of employing interference enhanced reflection as a detection means in the chemical substance detector of the present invention, it is particularly preferable since sensitivity is further increased.

Non-optical detection means can also be employed, as exemplified by electrical means and detection means that uses a crystal oscillator.

Interference enhanced reflection (IER) is a method that utilizes the reflection characteristic of a polymer film on a highly reflective substrate. Light reflected from the surface of a polymer film will interfere with light reflected at the interface between the polymer film and the substrate. The intensity of reflected light is largely dependent on the thickness and refractive index of the polymer film. Thus, the change in either the thickness of the polymer or its refractive index or the changes in both factors will appear as the change in the intensity of reflected light. Even in the case where a plurality of swollen polymer films behave differently, the degrees of swelling of the respective polymer films can be easily identified on the basis of the changes in the intensity of reflected light from the films. In short, the physical changes that occur in the chemical substance detecting film and which are used in IER are the changes in film thickness and refractive index.

Surface plasmon resonance (SPR) is a method in which light is incident on the metal-dielectric interface at the critical angle in such a way that the momentum and energy of photons at the interface will coincide with those of surface plasmons, whereby the metal-dielectric interface of interest can be excited optically. As a result, the energy of photons will couple with surface plasmons, causing a sharp drop in the intensity of reflected light. The efficiency of coupling with surface plasmons is greatly influenced not only by the thickness of the metal film but also by the characteristics of the dielectric on one side of the metal film. In short, the physical changes that occur in the chemical substance detecting film and which are used in SPR are also the changes in film thickness and refractive index.

In a preferred embodiment, the analyte or the substance that binds the analyte is labeled with a detectable label. The detectable label is often necessary because the results of specific binding reactions are frequently not directly observable. A variety of detectable labels have been devised for determining the presence of a reaction. Detectable labels have involved well known techniques including radiolabeling and the use of chromophores, fluorophores and enzyme labels. Radiolabels can be detected by radiation detectors. Chromophores and fluorophores have been detected by use of spectrophotometers or the naked eye. Redox active groups can be detected by electroanalytical methods. Biotin can be detected by its well-know binding to avidin or strepavidin. The avidin or strepavidin can itself be labeled with any of the labels described herein. Where members of a specific binding pair are tagged with an enzyme label, their presence may be detected by the enzymatic activation of a reaction system wherein a compound such as a dyestuff, is activated to produce a detectable signal.

Thus, in preferred embodiments, the label is a member selected from the group consisting of fluorescent groups, chromophoric groups, radioactive groups, redox active groups, biotin, enzyme labels and combinations thereof.

The labels in the present invention can be primary labels (where the label comprises an element which is detected directly) or secondary labels (where the detected label binds to a primary label, e.g., as is common in immunological labeling). An introduction to labels, labeling procedures and detection of labels is found in Polak et al., Introduction to Immunocytochemistry, $2^{nd}$ Ed., Springer Verlag, N.Y., (1977), and in Haugland, Handbook of Fluorescent Probes and Research Chemicals, a combined handbook and catalogue Published by Molecular Probes, Inc., Eugene, Oreg. (1996).

Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Greene™, rhodamine and derivatives (e.g., Texas red, tetrarhodimine isothiocynate (TRITC), etc.), dixogenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse-radish peroxidase, alkaline phosphatase etc.) spectral colorimetric labels such as colloidal gold or colored glass or plastic (e.g. polystyrene, polypropylene, latex, etc.) beads. The label can be coupled directly or indirectly to a component of the detection assay (e.g., a nucleic acid) according to methods well known in the art. As indicated above, a wide variety of labels can be used, with the choice of label depending on sensitivity required, ease of conjugation with the compound, stability requirements, available instrumentation, and disposal provisions.

In general, a detector which monitors an analyte is adapted to the particular label which is used. Typical detectors include spectrophotometers, phototubes and photodiodes, potentiostats, microscopes, scintillation counters, cameras, film and the like, as well as combinations thereof. Examples of suitable detectors are widely available from a variety of commercial sources known to persons of skill. Commonly, an optical image of an analyte comprising a bound label is digitized for subsequent computer analysis.

Preferred labels include those which utilize 1) chemiluminescence (using, for example, Horseradish Peroxidase and/or Alkaline Phosphatase with substrates that produce photons as breakdown products) with kits being available, e.g., from Molecular Probes, Amersham, Boehringer-Mannheim, and Life Technologies/ Gibco BRL; 2) color production [using both Horseradish Peroxidase and/or Alkaline Phosphatase with substrates that produce a colored precipitate] [kits available from Life Technologies/Gibco BRL, and Boehringer-Mannheim]; 3) hemifluorescence using, e.g., Alkaline Phosphatase and the substrate AttoPhos [Amersham] or other substrates that produce fluorescent products, 4) fluorescence [e.g., using Cy-5 [Amersham], fluorescein, and other fluorescent tags]; 5) radioactivity using, for example, kinase enzymes or other end-labeling approaches, nick translation, random priming, or PCR to incorporate radioactive molecules into the labeling nucleic acid; 6) redox labels using, for example, amino drugs labeled with cationic cobalocenium, procationic ferrocene or nitroxide groups (Limoges et al., *J. Electroanal. Chem.* 402: 175 (1996)), antibodies or enzymes labeled with ferrocene by reaction of n-(2-ferroceneethyl)maleimide with cysteine groups (Digleria et al. *FEBS Lett.* 390: 142 (1996), or 5-aminosalicylic acid as a redox-mediator for amperometric detection of enzymes labeled with horseradish peroxidase (Abdelhamid et al., *Electroanalysis* 10: 758 (1998). Other methods for labeling and detection will be readily apparent to one skilled in the art.

Fluorescent labels are highly preferred labels, having the advantage of requiring fewer precautions in handling, and being amenable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill.

Most typically, the amount of analyte present is measured by quantitating the amount of label fixed to the material of the invention following a binding event. Alternatively, the amount of material in the fluid can be quantitated. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes. Many other detection systems are widely available.

Immunological assays are of three general types. In competitive binding assays, labeled reagents and unlabeled analyte compounds compete for binding sites on a binding material such as that provided by the present invention. After an incubation period, unbound materials are washed off and the amount of labeled reagent bound to the site is compared to reference amounts for determination of the analyte concentration in the sample solution.

A second type of immunological assay is known as a sandwich assay and generally involves contacting an analyte sample solution to a surface, such as that of a material of the invention, comprising a first binding material immunologically specific for that analyte. A second solution comprising a labeled binding material of the same type (antigen or antibody) as the first binding material is then added to the assay. The labeled binding material will bind to any analyte which is bound to the first binding material. The assay system is then subjected to a wash step to remove labeled binding material which failed to bind with the analyte and the amount of labeled material remaining is ordinarily proportional to the amount of bound analyte.

A third type of immunological assay technique involves agglutination reaction techniques and is exemplified by well-known assays for blood antigens and serum types. Immunological cross-reactivity between antibodies within serum and antigens presented on red blood cell surfaces is indicated by the formation of a three dimensional cross-linked network of red blood cells and antibodies. The agglutination of the serum/red blood cell mixture results in the formation of a pellet which can be visible to the naked eye. The materials of the invention can be utilized, for example, to present the antibodies or the erythrocyte antigens.

These assay procedures, enumerated above, were originally performed according to liquid phase immunochemistry techniques wherein enzymes and radiolabeled reactions were carried out in liquid solution in apparatus such as microtiter plates. More recently, techniques and procedures have been adapted for carrying out "solid" phase assays wherein enzymatic and immunological reactions are carried out in solution on immobilizing substrates. The porous materials of the invention are well suited for use as an immobilizing substrate. Alternatively, the liquid phase immunochemical methods can be readily adapted to incorporate a material of the invention.

I. 5. Chiral Separations

The separation of enantiomeric mixtures into individual optical isomers is one of the most challenging problems in analytical and preparative chemistry, reflecting practical considerations important in many areas of science, particularly the pharmaceutical and agricultural industries.

The pharmaceutically active site of many drugs is "chiral," meaning that the active site is not identical to a mirror image of the site. However, many pharmaceutical formulations marketed today are racemic mixtures of the desired compound and its "mirror image." One optical form (or enantiomer) of a racemic mixture may be medicinally useful, while the other optical form may be inert or even harmful, as has been reported to be the case for thalidomide.

Chiral drugs are now extensively evaluated prior to large scale manufacturing, both to examine their efficacy, and to minimize undesirable effects attributable to one enantiomer or to the interaction of enantiomers in a racemic mixture. The United States Food and Drug Administration has recently issued new regulations governing the marketing of chiral drugs.

Separating optical isomers often requires considerable time, effort, and expense, even when state-of-the-art chiral separation techniques are used. There is a continuing and growing need for improved chiral separation techniques.

Early chiral separation methods used naturally occurring chiral species in otherwise standard separation protocols. For example, natural chiral polymeric adsorbents such as cellulose, other polysaccharides, and wool were used as early as the 1920's. Later strategies used other proteins and naturally occurring chiral materials. These early strategies gave some degree of success. However, the poor mechanical and chromatographic properties of naturally occurring materials often complicated the separations. Although naturally occurring chiral materials continue to be used for chiral separations, efforts have increasingly turned to synthesizing chiral materials having better mechanical and chromatographic properties. See, Armstrong, *Anal. Chem.* 59: 84A–91A 1987) gives a review of methods that have been used for chiral separations in liquid chromatography.

Thus, in an eighth aspect, the present invention provides a method for chiral separation comprising:

(a) contacting the chiral molecule with a multilayered porous material comprising;
   a porous substrate;
   a metal film adhered onto the substrate; and
   an organic layer attached to the metal film, the organic layer comprising a recognition moiety.

(e) forming a complex between the recognition moiety and the chiral molecule.

The two separation methods most often employed for chiral separations are high performance liquid chromatography and capillary electrophoresis, both of which have high efficiencies. High separation efficiencies are required for chiral separations because the difference in molar free energies of the interactions that discriminate between individual enantiomers is small, typically on the order of 100 calories per mole. The sum of the weighted time averages of these small interactions determines the overall enantioselectivity of a separation technique. High efficiencies are therefore required for chromatographic chiral separations. Separations on the order of 100,000 theoretical plates are readily achievable with capillary electrophoresis. Thus, small chiral selectivities can be magnified using capillary electrophoresis.

The so-called "three point rule" is a commonly used rule-of-thumb in many chiral recognition strategies. The "three point rule" recommends that there be a minimum of three simultaneous interactions between the chiral recognition medium and at least one of the enantiomers to be separated. In addition, at least one of the three interactions must be stereochemically dependent. The three interactions need not be attractive interactions, and may for example employ repulsion due to steric effects. For example, the "three point rule" was successfully used in 1971 in the design of a chiral stationary phase for the separation of the enantiomers of L-DOPA (L-dihydroxyphenylalanine). See, Baczuk et al., *J. Chromatogr.* 60: 351–361 (1971).

Until recently, the most common type of synthetic chiral stationary phase used in high performance liquid chromatography ("HPLC") was a Pirkle-type (Brush-type) phase. A Pirkle-type phase is based on the "three point rule," and usually employs pi-pi interactions (electron donor-acceptor) and intermolecular hydrogen bonding in chiral recognition. Thus, in a presently preferred embodiment, the materials of the invention form a complex with the analyte that is based on pi-pi interactions.

Another successful approach has used reversible complexes formed of metal ions and chiral complexing agents. This separation method is commonly called ligand-exchange-chromatography ("LEC"). LEC is usually explained by a model based on multicomponent complexes containing a central metal ion and two chelating chiral molecules. Enantiomers can be separated in LEC either by using chiral mobile phase additives, or by using a chiral stationary phase. In a further preferred embodiment, the materials of the invention form a complex with an analyte through a chiral recognition moiety and/or the method further comprises the use of a chiral additive to the fluid.

Host-guest enantioselective complexes, in either the mobile phase or the stationary phase, can also be used to separate individual enantiomers. Systems within this general category include those employing chiral crown ethers and cyclodextrins. Compared to crown ethers, cyclodextrins are relatively inexpensive, and are more readily derivatized. See, Gassmann et al., *Science* 230: 813–814 (1985); and Kuhn et al., *Chromatographia* 34: 505–512 (1992). For example, Armstrong et al., *Anal. Chem.* 59: 2237–2241 (1987) disclose the use of an aqueous liquid membrane employing cyclodextrin carriers to perform an enantiomeric enrichment. Additionally, Lakshmi et al., have recently discloses the resolution of a mixture of enantiomers by utilizing an apoenzyme that is selective for one of the enantiomer (Lakshmi et al., *Nature* 388(21), 758–760 (1997).

Thus, in a preferred embodiment, the present invention utilizes a recognition moiety that forms a complex by host-guest interactions with the analyte. In yet another preferred embodiment, the host-guest recognition moiety is a member selected from the group of crown ethers, cryptands and the like, cyclodextrins and biomolecules.

I. 6. Preparation of Mulilayered Membranes

In a ninth aspect, the present invention also provides a method of making the multilayered porous material of the invention. The method comprises, (a) contacting a porous substrate with a metal plating solution to form a porous substrate having a metal film adhered thereto;

(b) contacting the porous substrate having a metal film adhered thereto with a plurality of organic molecules that associate with the metal film, wherein at least a portion of said plurality of organic molecules comprise a member selected from the group consisting of recognition moieties, reactive moieties, protected reactive moieties and combinations thereof.

Any metal that can be plated, and preferably electrolessly plated, onto a porous substrate is useful in this aspect of the invention. Metals that are presently preferred as coatings include, but are not limited to, gold, silver, platinum, palladium, nickel and copper, more preferably gold and silver, and even more preferably, gold. In one embodiment, more than one metal is used. The more than one metal can be present as an alloy, they can be formed into a layered "sandwich" structure, or they can be laterally adjacent to one another.

Any electroless plating solution that can plate a metal onto a substrate can be used in practicing this aspect of the invention, however, solutions having certain characteristics are presently preferred. In a presently preferred embodiment, the plating solution comprises an easily reduced metal salt. In a preferred embodiment, a gold plating solution is utilized and the gold plating solution comprises a reducible gold salt. A presently preferred reducible gold salt is $Na_3Au(SO_3)_2$.

In another preferred embodiment, the metal plating solution further comprises a reducing agent. Reducing agents that are useful in this aspect of the invention include, hydroxylamine, oxalic acid, hydrazine, sodium borohydride and formaldehyde. A presently preferred reducing agent is formaldehyde.

The metal film can be plated directly onto the porous substrate, however, in a preferred embodiment, the method further comprises, prior to step (a), contacting a porous substrate with a sensitizer to form a sensitized porous substrate. In a preferred embodiment, the sensitizer is a transition metal salt. In a still further preferred embodiment, the sensitizer is a salt of $Sn^{+2}$.

Sensitizers are desirable for adjusting the surface character of the membranes. Sensitizers can improve the behavior of the substrate surface during plating. For example, it is known that, during the plating process, colloidal silica tends to aggregate or agglomerate when silver is electrolessly deposited. If the silica surface is first coated with, for example a complex oxide or a metal that forms a silicate (e.g., tin), the fine particles do not agglomerate.

In preferred embodiments, the metal salts used are soluble in water. Thus, salts such as metal chlorides, sulfates, nitrates, acetates and the like are particularly preferred. In other embodiments, the metal ion is complexed with an agent such as EDTA, tartrate and the like. The use of salts that are insoluble in water, but soluble in, for example, organic solvents (e.g. alcohols, DMSO, DMF, ethers, etc.), acids, bases and the like are also within the scope of the present invention.

In yet another preferred embodiment, when the outermost layer comprises gold, the method further comprises, prior to step (a), contacting the sensitized porous substrate with a silver solution to form a silver coated membrane. A presently preferred silver solution comprises $AgNO_3$. In a further preferred embodiment, the silver solution further comprises ammonia.

In certain preferred embodiments, a silver coated membrane is produced which is not then advanced to the gold plating stage. Silver coated membranes are useful when the porous material is used in combination with elevated temperatures, particularly when the organic layer comprises an organosulfur moiety: the silver-sulfur bond has been found to exhibit enhanced stability relative to the gold-sulfur bond at elevated temperatures.

As discussed above in the context of other aspects and embodiments of the invention, an array of organic layers and organic layer constituents can be used to practice this aspect of the invention. A preferred organic layer comprises an organosulfur moiety. In another preferred embodiment, the organic layer comprises a moiety selected from the group consisting of recognition moieties, reactive moieties, protected reactive moieties and combinations thereof.

When the organic layer comprises a reactive moiety, in a preferred embodiment, the method further comprises as step (d), reacting the reactive moiety with a recognition moiety. In another preferred embodiment, when the organic layer comprises a protected reactive moiety and the method further comprises, (d) deprotecting the protected reactive moiety to form a reactive moiety; and (e) reacting the reactive moiety with a recognition moiety. Many protecting groups and methods of attaching protecting groups to, and removing them from, reactive groups are known to those of skill in the art and one of skill will be able to ascertain appropriate groups and experimental conditions for a particular application.

J. Morphology

The porous materials can be used in a wide range of forms. Because the porous substrates can be shaped, bent molded, etc. into virtually any desired shaped and can be either planar or curved, the materials of the present invention can be produced in a wide range of shapes and sizes. The choice of appropriate shape and size will depend on the particular application for the materials of the invention and is well within the abilities of those of skill in the art.

In addition to size and shape, the pore size and pore density of the membranes can be selected from a wide array of combinations. Many commercially available membranes have appropriate pore sizes and pore densities for use in assembling the materials of the invention. If a porous substrate having a desired pore size and/or pore density is not commercially available, it is well within the abilities of those of skill in the art to prepare the necessary substrate.

K. Analytes

As discussed above, the materials and methods of the invention can be used to purify, separate, capture and/or detect any analyte, or class of analytes, which interacts with a recognition moiety. The interaction between the analyte and recognition moiety can be any physicochemical interaction, including covalent bonding, ionic bonding, hydrogen bonding, van der Waals interactions, repulsive electronic interactions, attractive electronic interactions and hydrophobic/hydrophilic interactions. In the following discussion, the materials and methods of the invention are discussed in terms of their ability to detect a substance or class of substances. The focus of this discussion is for reasons of clarity alone: the present materials and methods are equally applicable to purifying, excluding, capturing and assaying the analytes. Additional applications will be apparent to those of skill in the art and are encompassed within the scope of the present invention.

In a preferred embodiment, the interaction is an ionic interaction. In this embodiment, an acid, base, metal ion or metal ion-binding ligand is the analyte. In a still further preferred embodiment, the interaction is a hydrogen bonding interaction. In a particularly preferred embodiment, the hybridization of an immobilized nucleic acid to a nucleic acid having a complementary sequence is detected. In another preferred embodiment, the interaction is between an enzyme or receptor and a small molecule which binds thereto. One of skill in the art will appreciate that by judicious choice of recognition moiety, an analyte can be captured by, passed through or excluded by the membranes of the invention. For example, a complete strand of a nucleic acid can be separated from failure sequences by using its complementary strand as a recognition moiety. In one embodiment, the medium containing the complete strand is placed in a vessel divided into two compartments by the membrane and equilibrated with the membrane having the complementary strand as a recognition moiety. As the failure sequences will not anneal to the complementary strand with the same level of stability as the complete strand, the failure sequences can be passed through the membrane into the second compartment. After the failure sequences are eliminated, the ionic conditions or the temperature of the dialysis cell can be altered such that the complete strand is separated from the membrane and can be isolated.

In another embodiment, the analyte competes for the recognition moiety with another agent that has been bound to the recognition moiety prior to introducing the analyte of interest. In this embodiment, it is the process or result of the analyte displacing the pre-bound agent that causes the detectable signal. Suitable combinations of recognition moieties and analytes will be apparent to those of skill in the art. In a preferred embodiment, the displaced species diffuses through the membrane and is detected by an agent that is selective for the displaced species. This embodiment is discussed in greater detail in section I.4, above.

In presently preferred embodiments, the analyte is a member selected from the group consisting of acids, bases, organic ions, inorganic ions, pharmaceuticals, herbicides, pesticides, chemical warfare agents, noxious gases and biomolecules. Importantly, each of these agents can be purified, captured and/or detected as a gas, vapor or a liquid. These agents can be present as components in mixtures of structurally unrelated compounds, racemic mixtures of stereoisomers, non-racemic mixtures of stereoisomers, mixtures of diastereomers, mixtures of positional isomers or as pure compounds. Within the scope of the invention is a device and a method to purify, capture and/or detect a particular analyte of interest without interference from other substances within a mixture.

Both organic and inorganic acids can be detected using the device and method of the present invention. In a preferred embodiment, the recognition moiety comprises a group which is protonated by the acid. Alternatively, the recognition moiety can be one that is not protonated by the acid, but is acidic itself and, thus, excludes the acid from the membrane by a repulsive interaction. The use of such repulsive interactions to exclude species from the membrane can be used with substantially all of the analytes with which the present invention can be practiced.

In another preferred embodiment, the invention provides a material and a method for detecting bases. The methods and methods applicable to bases are substantially similar to those discussed above in the context of acids; the notable exception being that the base will preferably deprotonate a group on a SAM component, spacer arm or metal film. When the base is negatively charged, preferred recongition moieties are positively charged.

Organic ions which are substantially non-acidic and non-basic (e.g., quaternary alkylammonium salts) can be purified, captured, detected by or excluded from the materials of the invention. For example, a recognition moiety with ion exchange properties is useful in the present invention. A specific example is the exchange of a cation such as dodecyltrimethylammonium cation for a metal ion such as sodium. Recognition moieties that form inclusion complexes with organic ions are also of use. For example, crown ethers and cryptands can be used to form inclusion complexes with organic ions such as quaternary ammonium cations.

Inorganic ions such as metal ions and complex ions (e.g., $SO_4^{-2}$, $PO_4^{-3}$) can also be detected using the device and method of the invention. Metal ions can be detected, for example, by their complexation or chelation by agents bound to a SAM component, spacer arm or the substrate. In this embodiment, the recognition moiety can be a simple monovalent moiety (e.g., carboxylate, amine, thiol) or can be a more structurally complex agent (e.g., ethylenediaminepentaacetic acid, crown ethers, aza crowns, thia crowns).

Complex inorganic ions can be detected by their ability to compete with ligands for bound metal ions in ligand-metal complexes. When a ligand bound to a SAM component, a spacer arm or a substrate forms a metal-complex having a thermodynamic stability constant which is less than that of the complex between the metal and the complex ion, the complex ion will cause the dissociation of the metal ion from the immobilized ligand.

The dissociation of the metal-complex can be used to create a signal in, for example, a chamber of a dialysis vessel, wherein the membrane divides the vessel into two or more chambers. The amount of metal ion displaced from the bound ligand, and hence the magnitude of the signal, will be dependent on the stability constant of the metal-complex and the concentrations of the constituents. Thus, the materials and the methods of the invention can be used to assay a metal-complex for its relevant stability constant(s). Methods of determining stability constants for compounds formed between metal ions and ligands are well known to those of skill in the art. Using these stability constants, membranes and devices which are specific for particular ions can be manufactured. Metal containing species can be detected by, for example, detecting changes in a chromophore or fluorophore. Alternatively, the detection can utilize colorimeteric, potentiometric, coulometric and other methods. See, Martell, A. E., Motekaitis, R. J., Determination and Use of Stability Constants, 2d Ed., VCH Publishers, New York 1992.

Small molecules such as drugs, pesticides, herbicides, agents of war, and the like can be detected by the use of a number of different recognition moiety motifs. Acidic or basic components can be detected as described above. An agent's metal binding capability can also be used to advantage, as described above for complex ions. Additionally, if these agents bind to an identified biological structure (e.g., a receptor, antibody, etc.), the receptor can be immobilized on the membrane. Techniques are widely available in the art for raising antibodies that are highly specific for a particular small molecule. Thus, it is within the scope of the present invention to make use of antibodies against small molecules for detection of those molecules.

In yet another embodiment, a receptor, an enzyme or antibody is located in a chamber of a dialysis vessel. The membrane divides the dialysis vessel into two or more chambers. As a molecule that the antibody binds to passes through the membrane, its binding to the antibody can be detected. Detection methods known in the art as well as those discussed herein are generally applicable to this method as well.

In a preferred embodiment, the affinity of an analyte for a particular metal ion is exploited by having a membrane labeled with an immobilized metal ion. The metal ion generally must have available at least one empty coordination site to which the analyte can bind. Alternatively, at least one bond between the metal and the metal-immobilizing agent must be sufficiently labile in the presence of the analyte to allow the displacement of at least one bond of the immobilizing reagent by the analyte.

The binding of this metal ion to the analyte can be detected by a number of methods. In one embodiment, the binding results in a change that is detected electronically (e.g., potentiometrically, etc.).

In a preferred embodiment, the agent detected by binding to an immobilized metal ion is an organophosphorous compound such as a nucleic acid, an insecticide or an agent of war (e.g., VX, O-ethyl-S-(2-diisopropylaminoethyl)-methylthiophosphonate). Exemplary compounds which exhibit affinity for organophosphorous agents include, but are not limited to, $Cu^{+2}$-diamine, triethylentetraamine-$Cu^{+}$ 2-chloride, tetraethylenediamine-$Cu^{+2}$-chloride and 2,2'-bipyridine-$Cu^{+2}$-chloride. See, U.S. Pat. No. 4,549,427, issued to Kolesar, Jr., E. S. on Oct. 29, 1985.

In another preferred embodiment, antibodies to the particular agents are immobilized on the membrane. Techniques for raising antibodies to herbicides, pesticides and agents of war are known to those of skill in the art. See, Harlow, Lane, Monoclonal Antibodies: A Laboratory Manual, Cold Springs Harbor Laboratory, Long Island, N.Y., 1988.

In a preferred embodiment, the nucleic acids that are detected include RNA and DNA both as single molecules and as hybrids with one or more complementary strands of another nucleic acid is within the scope of the invention.

In a preferred embodiment, the herbicides are preferably members of the group consisting of triazines, haloacetanilides, carbamates, toluidines, ureas, plant growth hormones and diphenyl ethers. Included within these broad generic groupings are commercially available herbicides such as phenoxyl alkanoic acids, bipyridiniums, benzonitriles, dinitroanilines, acid amides, carbamates, thiocarbamates, heterocyclic nitrogen compounds including triazines, pyridines, pyridazinones, sulfonylureas, imidazoles, substituted ureas, halogenated aliphatic carboxylic acids, inorganics, organometallics and derivatives of biologically important amino acids.

In the embodiments discussed above, the preferred agent of war is a member of the group consisting of mustard and related vesicants including the agents known as HD, Q, T, HN1, HN2, HN3, nerve agents, particularly the organic esters of substituted phosphoric acid including tabun, sarin, isopropyl methylphosphonofluoridate, soman pinacolyl methylphosphonofluoridate. Other detectable analytes include incapacitants such as BZ, 3-quinuclidinyl benzilate and irritants such as the riot control compound CS.

Pesticides preferred for detection using the present invention include bactericides (e.g., formaldehyde), fumigants (e.g., bromomethane), fungicides (e.g., 2-phenylphenol, biphenyl, mercuric oxide, imazalil), acaricides (e.g., abamectin, bifenthrin), insecticides (e.g., imidacloprid, prallethrin, cyphenothrin).

The present invention also provides a device and a method for detecting noxious gases such as CO, $CO_2$, $SO_3$, $H_2SO_4$, $SO_2$, NO, $NO_2$, $N_2O_4$ and the like. In a preferred embodiment, membrane includes at least one compound capable of detecting the gas. Useful compounds include, but are not limited to, palladium compounds selected from the group consisting of palladium sulfate, palladium sulfite, palladium pyrosulfite, palladium chloride, palladium bromide, palladium iodide, palladium perchlorate, palladium complexes with organic complexing reagents and mixtures thereof. In a preferred embodiment, the gas is detected by a change in an electrical property of the membrane. Methods of measuring current and/or voltage changes across a metallic surface are well known to those of skill in the art.

Other compounds of use in practicing this embodiment of the present invention include, molybdenum compounds such as silicomolybdic acid, salts of silicomolybdic acid, molybdenum trioxide, heteropolyacids of molybdenum containing vanadium, copper or tungsten, ammonium molybdate, alkali metal or alkaline earth salts of molybdate anion, heteropolymolybdates and mixtures thereof.

Still further useful gas detecting compounds include, copper salts and copper complexes with an available coordination site. Alpha-cyclodextrin, beta-cyclodextrin, modified alpha- and beta-cyclodextrins, gamma-cyclodextrin and mixtures thereof are of use in practicing the present invention. See, U.S. Pat. No. 5,618,493, issued to Goldstein et al. on Apr. 8, 1997 and U.S. Pat. No. 5,071,526, issued to Pletcher et al. on Dec. 10, 1991.

In another preferred embodiment, the gas the membrane is derivatized with a compound selected from the group consisting of amorphous hemoglobin, crystalline hemoglobin, amorphous heme, crystalline heme and mixtures thereof. The heme serves as a recognition moiety which is reactive towards the gas. See, U.S. Pat. No. 3,693,327, issued to Scheinberg, I. A. on Sep. 26, 1972.

When the analyte is a biomolecule, any recognition moiety which interacts with the biomolecule is useful in practicing the present invention. Thus, when the analyte is a nucleic acid, in one embodiment, the recognition moiety is a nucleic acid having a sequence which is at least partially complementary to the recognition moiety sequence. When the recognition moiety is a peptide, an antibody specific for that peptide can be used as the analyte. In another preferred embodiment, a protein, other than an antibody (e.g., enzyme, receptor) is the analyte. The binding of biomolecules to the membrane can be detected by detection methods substantially similar to those discussed herein.

Other combinations of analytes and recognition moieties and other detection schemes will be apparent to those of skill in the art.

L. Drug Delivery Devices

Presently there are two types of transdermal drug delivery systems, i.e., passive and iontophoretic. Passive patch systems deliver small and relatively lipophilic drugs through the skin of the patient by diffusion, an example of which would involve the application of a narcotic analgesic patch to provide pain relief. Iontophoresis systems, on the other hand, deliver drug through the skin of the patient through the application of an electromotive force (iontophoresis) to drive ionizable substances (medicament) into the skin so that they can be absorbed by adjacent tissues and blood vessels. Iontophoresis, therefore, allows charged and hydrophilic drugs to be transported across the skin which are poorly deliverable through passive diffusion. Transdermal systems offer advantages clearly not achievable by other modes of administration, such as hypodermic injection which has the associated problem of pain, risk of infection and trauma to the patient. Iontophoresis also has advantages over oral administration in that introduction of the drug through the gastrointestinal tract may result in inactivation of the medicament, food interactions, first pass hepatic metabolism and gastrointestinal side effects.

Thus, in a ninth aspect, the present invention provides a drug delivery device comprising:

(a) a porous substrate;
(b) a metal film adhered onto said substrate;
(c) an organic layer attached to said metal film, said organic layer containing a recognition moiety; and
(d) a drug moiety reversibly associated with said recognition moiety.

The devices of the invention can operate by passive diffusion or iontophoresis. In a preferred embodiment, the device operates by ionotphoresis.

Iontophoretic drug delivery systems, have, in recent years, become an increasingly important means of administering drugs. Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification 410,009 (1934) describes an iontophoric device which overcame one of the disadvantages of such early devices known to the art at that time, namely the requirement of a special low tension (low voltage) source of current which meant that the patient needed to be immobilized near such source. The device of that British specification was made by forming from the electrodes and the material containing the medicament or drug to be delivered transdermally, a galvanic cell which itself produced the current necessary for iontophoretically delivering the medicament. This ambulatory device thus permitted iontophoretic drug delivery with substantially less interference with the patient's daily occupation.

More recently, a number of U.S. patents have issued in the iontophoresis technology, indicating a renewed interest in this mode of drug delivery. For example, U.S. Pat. No. 3,991,755 issued to Jack A. Vernon et al;. U.S. Pat. No. 4,141,359 issued to Stephen C. Jacobson et al;. U.S. Pat. No. 4,398,545 issued to Wilson; U.S. Pat. No. 4,250,878 issued to Jacobsen disclose examples of iontophoretic devices and some applications thereof. The iontophoresis process has been found to be useful in the transdermal administration or introduction of medicaments or drugs including lidocaine hydrochloride, hydrocortisone, acetic acid, fluoride, penicillin, dexamethasone sodium phosphate and many other drugs. Perhaps the widest use of iontophoresis is that of diagnosing cystic fibrosis by using pilocarpine nitrate iontophoresis. The pilocarpine nitrate stimulates sweat production; the sweat is collected and analyzed for its chloride content to detect the presence of the disease.

Conventional iontophoretic devices, such as those described in U.S. Pat. No. 4,820,263 (Spevak, et al.), U.S. Pat. No. 4,927,408 (Hank, et al.) and U.S. Pat. No. 5,084,008 (Phipps), the disclosures of which are hereby incorporated by reference, provide for delivery of a drug or medicament transdermally through iontophoresis. Basically, conventional iontophoretic devices consist of a power source connected to two electrodes, an anode and a cathode, which are individually in ionic contact with an electrolyte or drug reservoir which is in contact with the skin to be treated by the iontophoretic device. When the current is turned on, electrical energy is used to assist in the transport of ionic molecules into the body through the skin, via ionic conduction.

The iontophoretic electrode of the invention includes a current distributing member such as the multilayered porous of the materials of the invention which conveys electrical current into iontophoretic reservoirs for the delivery of an ionized substance. The current distributing member is constructed of any of a large variety of electrically conductive materials, including both inert and sacrificial materials.

Inert conductive materials are those electrically conductive materials which, when employed in the iontophoretic devices of the invention, do not themselves undergo or participate in electrochemical reactions. Thus, an inert material distributes current without being eroded or depleted due to the distribution of current, and conducts current through the generating ions by either reduction or oxidation of water. Inert conductive materials typically include, for example, stainless steel, platinum, gold, and carbon or graphite. The inert conductive material can be a constituent of the porous substrate, the metal film or both of these components. In a preferred embodiment, a metal film is used as the inert conductive component.

Alternatively, the current distributing member can be constructed from a sacrificial conductive material. A material is considered sacrificial if, when employed as an electrode in an iontophoretic device of the invention, the material is eroded or depleted due to its oxidation or reduction. Such erosion or depletion occurs when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

In the device of the invention, the sacrificial layer can be any component of the multilayered material. In a preferred embodiment, the sacrificial material is the porous substrate, a metal film or a combination of the two components.

In presently known iontophoretic devices, at least two electrodes are generally used. Both these electrodes are disposed so as to be in intimate electrical contact with some portion of the skin of the body. One electrode, called the active electrode, is the electrode from which the ionic substance, medicament, drug precursor or drug is delivered or driven into the body by electrical repulsion. The other electrode, called the indifferent or ground electrode, serves to close the electrical circuit through the body. In conjunction with the patient's skin contacted by the electrodes, the circuit is completed by connection of the electrodes to a source of electrical energy, e.g., a battery, or appropriately modified household current. For example, if the ionic substance to be driven into the body is positively charged, then the positive electrode (the anode) will be the active electrode and the negative electrode (the cathode) will serve to complete the circuit. If the ionic substance to be delivered is negatively charged, then the negative electrode will be the active electrode and the positive electrode will be the indifferent electrode.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate electrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context.

M. Compositions, Kits and Integrated Systems

The invention provides compositions, kits and integrated systems for practicing the various aspects and embodiments of the present invention, including producing the porous materials and performing the methods.

The invention provides kits for practicing the methods noted above. The kits can include any of the materials noted above, and optionally further include additional components such as instructions to practice the methods, one or more containers or compartments (e.g., to hold the porous material, nucleic acids, antibodies, inhibitors or the like), or the like.

The invention also provides integrated systems for performing the methods disclosed herein. For example, in performing assays, in one embodiment, the delivery of individual compounds or compound components is accomplished by means of a robotic armature which transfers fluid from a source to a destination, a controller which controls the robotic armature, a label detector, a data storage unit which records label detection, and an assay component such as a microtiter dish comprising a well comprising the multilayered porous material, or a substrate comprising a fixed multilayered porous material. When a labeled compound is used, it is detected by means of the label detector.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous ligation reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip- compatible DOS™, OS2™ WINDOWS™, WINDOWS NT™ or WINDOWS95™ based machines), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of porous material) are sampled to obtain light intensity readings for each position. Multiple pixels are processed in parallel to increase speed. The apparatus and methods of the invention are easily used for viewing any sample, e.g., by fluorescent or dark field microscopic techniques.

The materials, methods and devices of the present invention are further illustrated by the examples that follow. These examples are offered to illustrate, but not to limit the claimed invention.

EXAMPLES

The procedure for preparation and the structure of an exemplary membrane of the invention is illustrated in FIG. 1. Any kind of filtration membrane with approximately uniform pore sizes and suitable chemical properties can be used as templates. PCTE membranes (Poretics, Inc.) were chosen as an exemplary membrane substrate. These membranes contain cylindrical pores with uniform pore sizes. The pores are nearly perpendicular to the membrane surfaces. Electroless gold was deposited on the pore walls and both faces of the membrane using a procedure similar to that reported by Martinet al. (Menon, V. P. et al., *Anal. Chem.* 1995, 67, 1920–1928). Self-assembled monolayers were then formed from functionalized alkanethiols on the surface of deposited gold to introduce ionizable groups into the membrane. Since the a thickness of gold may not be the same throughout the whole pore (a bottle-neck structure is usually formed near the ends of the pore (Jirage, K. B. et al., *Science* 1997, 278, 655–658).

After deposition of electroless gold at 0–2° C. for 4.5 hours, the amount of deposited gold was ~0.25 mg per $cm^2$ of membrane and the apparent pore radius was reduced to 16 nm (measured by water flux). The apparent pore radius was reduced to 14 mn (measured by water flux) after SAMs were formed from $HS(CH_2)_{15}COOH$ onto deposited gold. The 2 nm reduction of pore radius corresponds to the chain length of the adsorbed thiol molecules.

EXAMPLE 1

1.1a Characterization of the Membranes

The PCTE membrane pore radius was determined by water flux under a pressure drop across the membrane. The pore density of the membranes was determined by SEM images [Kim, K. J.,; Stevens, P, V., *J Membr. Sci.* 1997, 123, 303–314] is 7.7±2.4 pores/$\mu m^2$. Since image analysis usually induces systematic errors, the pore density utilized was that provided by the manufacture (6 pores/$\mu m^2$) calculations of pore radius from water flux experiments and apparent diffusivities from diffusion experiments.

The determined value of pore radius (32 nm), however, was more than twice of the value labeled by the manufacturer (15 nm). Similar discrepancy was revealed in a recent report [Kim, K. J.; Stevens, P. V., *J Membr. Sci.* 1997, 123, 303–314], where the pore radius measured by water flux under a pressure drop of 100 kPa was more than four times of the labeled value. The discrepancy was attributed to the expansion of pores under stress (by pressure drop). The pressure drop applied in the present experiments (~2 kPa), however, was much smaller. The larger measured pore radius compared to the manufacturer's stated value might be caused by deformation of pores due to swelling of polycarbonate in water.

1.1b Electroless Deposition of Gold

A PCTE membrane as purchased was first conditioned in a solution of 0.026 M tin (II) chloride and 0.07 M trifluoroacetic acid for 3 minutes. The solvent of this solution was a 1:1 mixture of water and methanol. This step allowed $Sn^{2+}$ to be adsorbed to the pore walls and the surfaces of the membrane. The tin-sensitized membrane was rinsed thoroughly with methanol and then immersed into an aqueous solution of ammoniacal silver nitrate (0.03 M) for 2 minutes. In this step, a redox reaction leaded to the decoration of the membrane with a layer of silver. The membrane was then rinsed with methanol and subsequently with water. Finally, the silver-decorated membrane was immersed into a gold plating solution containing 7.9 mM $Na_3Au(SO_3)_2$ (diluted from Oromerse Part B, Technic, Inc.), 0.127 M sodium sulfite, and 0.625 M formaldehyde. Deposition of elemental gold was carried out in this solution. The temperature of this solution was maintained around 0–2° C., at which the rate of deposition of gold was estimated to be 4–5 nm/hr. Variation of deposition time resulted in different pore sizes. After deposition was finished, the membrane was thoroughly rinsed with water.

1.1c Treatment of Electroless Gold

The gold-coated PCTE membrane was immersed in 25% nitric acid for 12 hours to clean the deposited gold. This treatment was necessary for the formation of close-packed SAMs onto the gold (Hou, Z. et al., *Langmuir*, in press). The membrane was then thoroughly rinsed with water and air-dried.

1.1c Formation of SAMS

The gold-coated PCTE membrane was rinsed with ethanol before immersion in an ethanolic solution of a functionalized alkanethiol (~1 mM) for at least 12 hours. The membrane was then rinsed with ethanol and dried. The pore size of the fabricated membrane could be further reduced by using alkanethiols with long chains.

We fabricated a pH-responsive ion-exchange membrane beating carboxylic acid groups by electroless deposition of gold on PCTE membrane and self-assembly of 15-mercaptohexadecanoic acid [$HS(CH_2)_{15}COOH$, Aldrich] onto deposited gold following the above procedure.

EXAMPLE 2

Example 2 demonstrates the ability of the membranes of the invention to provide ion selective ion transport between two chambers of a diffusion apparatus.

Figure 2:
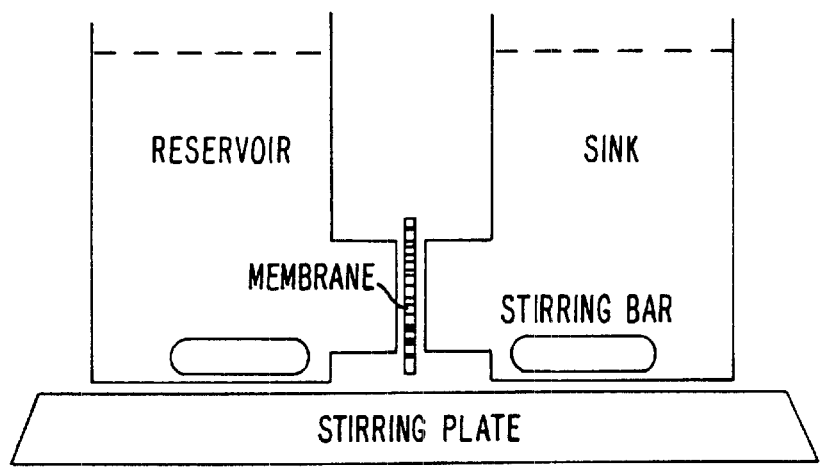
FIG. 2 is a diagram of a diffusion cell incorporating a membrane of the invention.

The membrane described in Example 1, was used to separate two compartments (reservoir and sink) in a diffusion cell (FIG. 2). The effective area of the membrane was 1.77 $cm^2$. Before each diffusion experiment started, the reservoir contained a solution (45 ml) of 1 mM potassium permanganate ($KMnO_4$), while the sink contained a blank solution (45 ml) with no KMnO4. The pH of solutions in both reservoir and sink was adjusted to a desired value by adding the same amount (0–0.04 mM) of sulfuric acid (or potassium hydroxide, 0–0.1 mM) to the solutions in the reservoir and the sink.

To remove the effect of any change of ionic strength due to variation of pH on electrical double layer forces, the same amount of potassium nitrate was added to the solutions in both the reservoir and the sink to maintain the ionic strength of the solution in the reservoir (~1.1 mM) and that in the sink (~0.1 mM) at constant values.

The membrane had been conditioned in a solution that was the same as the solution in the sink in the subsequent diffusion experiment for at least 1 hour. Vigorous stirring (at the same speed setting) was applied in both compartments in all diffusion experiments by using two magnetic stirrers and a Corning stirring plate (FIG. 2). A small amount of solution (~1 ml) was periodically sampled from the sink and the concentration of $MnO_4^-$ was determined by absorbance measured at 525 nm. Each sample solution was returned to the sink immediately after measurement (which took 1–2 min). The concentration of $MnO_4^-$ in the reservoir decreased by less than 0.2% during each diffusion experiment and thus could be considered constant. The flux of $MnO_4^-$ across the membrane was determined by the change of the concentration of $MnO_{4-}$ in the sink with time:

$$J = \frac{C_s V}{(\pi R^2 A \delta)t}$$

where $C_s$ is the concentration of $MnO_4$ in the sink measured at time t ($C_s/t$ was obtained from the plot of Cs against t), V is the volume of solution in the sink, and A is the effective area of the membrane. R, L, and σ are the radius, length, and number density (per unit area of membrane) of the pores, respectively.

Figure 3:
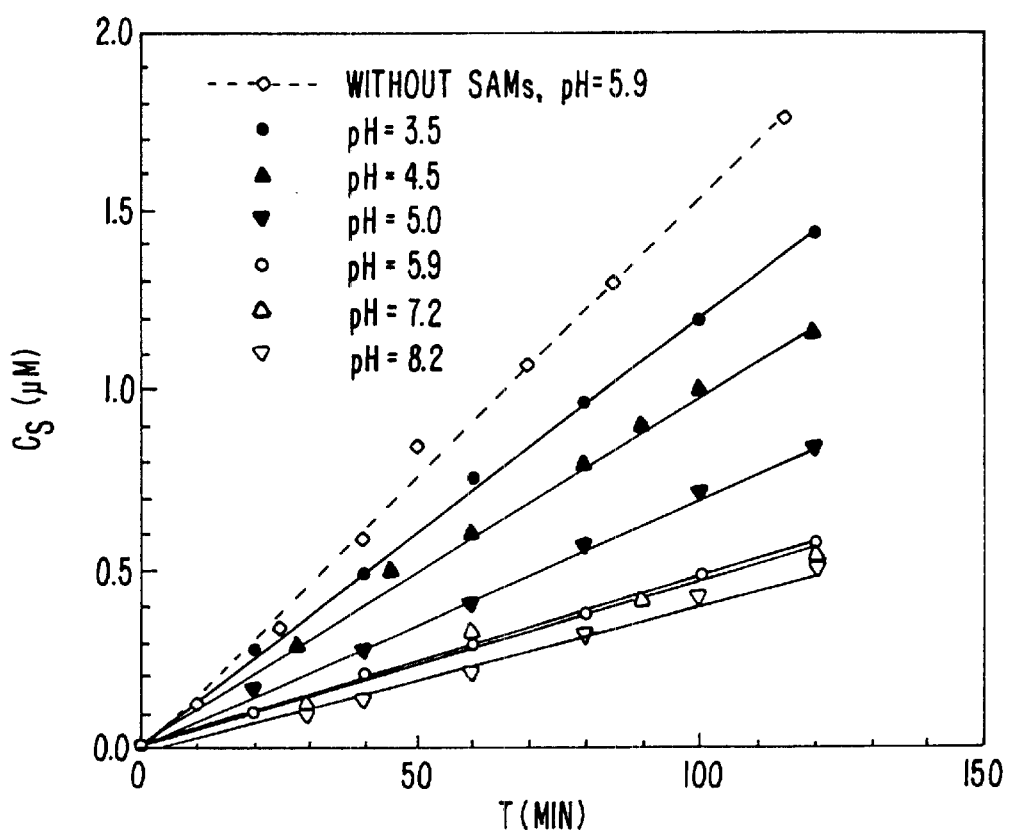
FIG. 3 is a display of the changes in concentration of $MnO_4^-$ in the sink at different external pH values during diffusion experiments using the membranes carboxylic acid groups (except the dashed line). The concentration of $MnO_4^-$ in the reservoir is 1 mM.

The changes of concentrations of $MnO_4$ in the sink with time observed at different external pH values in the diffusion experiments are shown in FIG. 3. The slope of each line is proportional to the flux of $MnO_4^-$ passing through the membrane. The dashed line in FIG. 3 was obtained by measuring $C_s$ at pH 5.9 before SAMs were on the pore walls. The value of Cs, measured at 40 min when the pH was changed to 3.6 or 8.0 was the same as that at pH 5.9. The slope of this line is larger than those measured after the formation of the SAMS. In the latter case, higher pH values result in smaller fluxes of $MnO_4^-$. This phenomenon is consistent with pH dependent ionization of the terminal carboxylic groups in the SAMs and electrostatic interactions between the surface charge on the pore walls and the $MnO_4^-$ anion. The higher the pH, the larger the density of fixed negative charges due to more ionized carboxylic groups on the pore walls, and consequently the more $MnO_4^-$ anions are electrically excluded from the pores.

Figure 4:
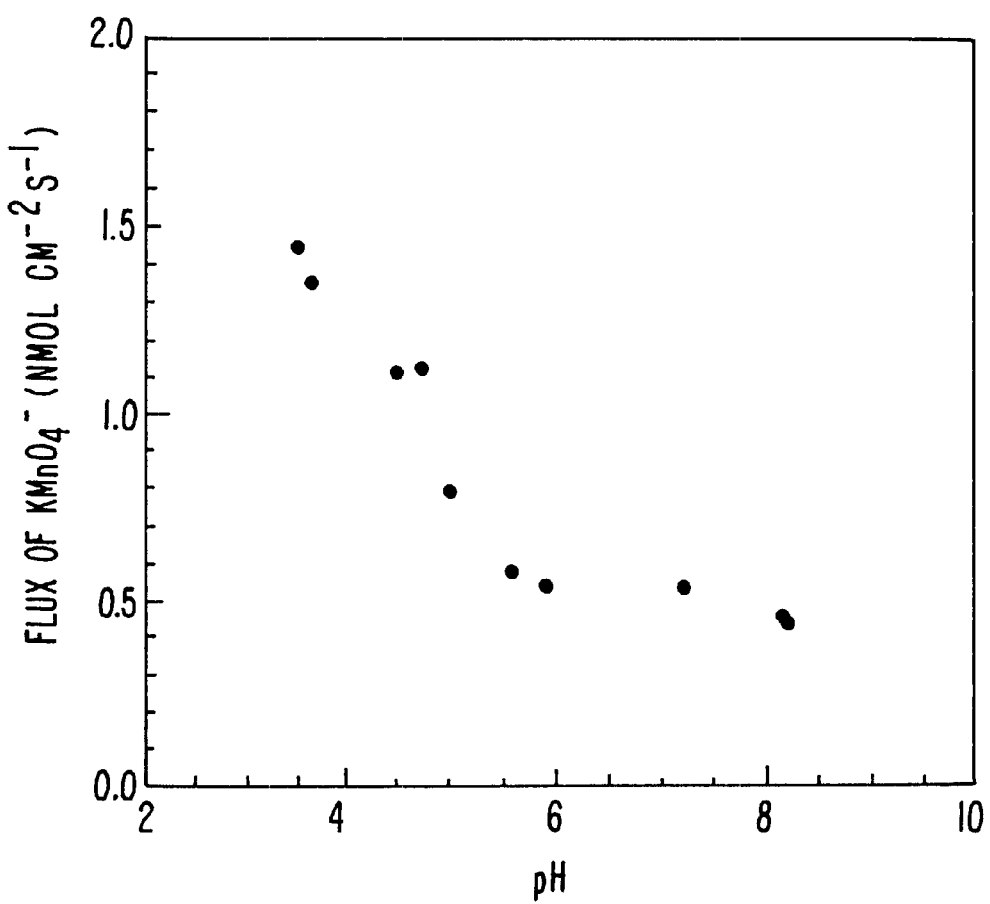
FIG. 4 is a plot of the flux of MnO4— across the membrane bearing carboxylic acid groups as a function of external pH. The concentration of MnO4— in the reservoir is 1 mM.
Figure 5A:
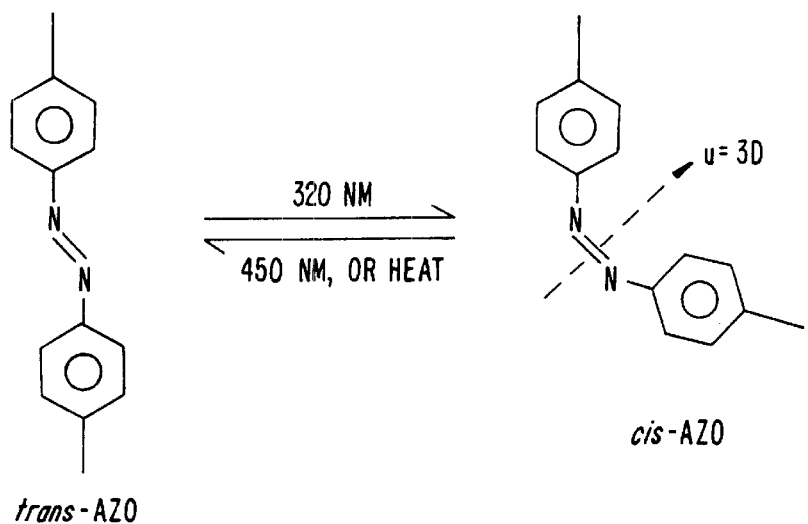
FIG. 5 is a schematic illustration of a light-controllable membrane: (a) configuration change of a azobenzene group embedded in a chain; (b) light-responsive adjustment of the size of the pore with SAMs formed from azobenzene-containing functionalized molecules onto the pore wall.
Figure 5B:
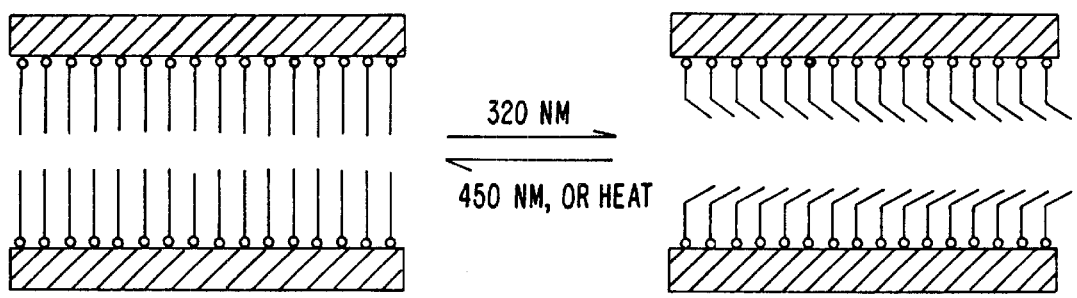

FIG. 4 gives the flux of $MnO_4^-$ across the membrane bearing the carboxylic acid groups as a function of the external pH. The value of the flux at pH 3.5 is three times the value at pH 8.2. The flux drops by a factor of 2.5 as the pH changes from 3.5 to 5.5 and decreases slightly when the pH is higher than 6. The pH was changed between high values and low values alternatively. The property of pH-dependent transport of $MnO_4^-$ did not change during the cumulative time of ~30 hours of diffusion experiments with feeding solutions of 1 mM $KMnO_4$.

The Debye length corresponding to the ionic strength (~1.1 mM) of the solution in the reservoir is ~9.1 nm. This is smaller than the pore radius (14 nm). Under the above conditions, the partitioning coefficient of the anion (defined by the ratio of the average concentration of the ion in a pore to that outside the pore) at high external pH values (>8.0) is estimated to be ~0.12. This nonnegligible value of partitioning coefficient may be the reason why the permeation of $MnO_4$ is not completely inhibited even when most of the terminal carboxylic groups are dissociated at high pH values shown in FIG. 4. There should be no effect of association of $MnO_4^-$ on the flux of $MnO_4^-$ because the low $pK_a$ value of $MnO_4^-$ (~2.2) ensures that $MnO_4^-$ is completely dissociated in the whole range of pH shown in FIG. 4.

It is understood that the examples and embodiments described herein are for illustrative purposes only and that various modifications or changes in light thereof will be suggested to be persons skilled in the art and are to included within the spirit and purview of this application and are considered within the scope of the appended claims. All publications, patents, and patent applications cited herein are hereby incorporated by reference in their entirety for all purposes.

What is claimed is:

1. A multilayered porous membrane comprising:
   (a) a porous substrate;
   (b) a metal film adhered onto said substrate; and
   (c) an organic layer attached to said metal film, said organic layer having a recognition moiety attached thereto,
   wherein said membrane is porous.

2. The material according to claim 1, wherein said substrate is a member selected from the group consisting of optically opaque substrates, optically transparent substrates, insulating substrates, conducting substrates, semiconducting substrates, magnetic substrates and combinations thereof.

3. The material according to claim 1, wherein said substrate is a member selected from the group consisting of metals, inorganic oxides, inorganic glasses, organic polymers and combinations thereof.

4. The material according to claim 3, wherein said organic polymer is a member selected from the group consisting of polypropylene, nylon, fluorocarbon, polyester, polyethylene, polysulfone, polyether sulfone, cellulose, cellulose ester, ethyl vinyl acetate, polycarbonate, polyaramide, polyimide and combinations thereof.

5. The material according to claim 3, wherein said metal is a member selected from the group consisting of nickel, copper, silver, gold, platinum, palladium and combinations thereof.

6. The material according to claim 3, wherein said inorganic oxide is a member selected from the group consisting of silicon polymers, $ZnO$, $TiO_2$, $Fe_2O_3$, $Al_2O_3$, $CeO_2$, $SnO_2$, $CuO$, $Cr_2O_3$, $SiO_2$ and combinations thereof.

7. The material according to claim 1, wherein said substrate is track-etched.

8. The material according to claim 1, wherein said metal film is a member selected from the group consisting of nickel film, copper film, silver film, gold film, platinum film, palladium film and combinations thereof.

9. The material according to claim 8, wherein said metal film is a gold film.

10. The material according to claim 1, wherein said metal film is layered onto said substrate by electroless deposition.

11. The material according to claim 1, wherein said organic layer is attached to said metal film through a mechanism which is a member selected from the group consisting of covalent bonding, ionic bonding, coordination, van der Waals interactions, chemisorption, physisorption and combinations thereof.

12. The material according to claim 1, wherein said organic layer comprises an organosulfur moiety.

13. The material according to claim 12, wherein said organic layer comprises a group having the structure:

—SR$^1$(X$^1$)$_n$ wherein
   R$^1$ is a linking group between sulfur and X$^1$;
   X$^1$ is a member selected from the group consisting of H, halogen, recognition moieties, hydrophilic polymers and combinations thereof;
   n is a number between 1 and 50.

14. The material according to claim 13, wherein R$^1$ is a member selected from the group consisting of stable linking groups and cleaveable linking groups.

15. The material according to claim 14, wherein R$^1$ is a stable linking group which is a member selected from the group consisting of alkyl, substituted alkyl, aryl, arylalkyl, substituted aryl, substituted arylalkyl, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups.

16. The material according to claim 15, wherein R$^1$ is a member selected from the group consisting of alkyl and substituted alkyl groups.

17. The material according to claim 14, wherein R$^1$ is a cleaveable linking group comprising a cleaveable moiety which is a member selected from group consisting of disulfide, ester, imide, carbonate, nitrobenzyl, phenacyl and benzoin groups.

18. The material according to claim 13, wherein said organic layer comprises:

X$^1$Q$_2$C(CQ$^1{}_2$)$_m$(Z$^1$)$_o$(CQ$^2{}_2$)$_n$S— wherein,
   X$^1$ is a member selected from the group consisting of H, OH, halogen and recognition moieties;
   Q, Q$^1$ and Q$^2$ are independently members selected from the group consisting of H and halogen;
   Z$^1$ is a member selected from the group consisting of —CQ$_2$—, —CQ$^1{}_2$—, —CQ$^2{}_2$—, —O—, —S—, —NR$^1$—, —C(O)NR$^1$ and R$^1$NC(O)—,
   in which;
      R$^1$ is a member selected from the group consisting of H, alkyl, substituted alkyl, aryl, substituted aryl, heteroaryl and heterocyclic groups;
      m is a number between 0 and 40; and
      n is a number between 0 and 40;
      o is a number between 0 and 5.

19. The material according to claim 18, wherein Q, Q$^1$ and Q$^2$ are independently members selected from the group consisting of H and fluorine.

20. The material according to claim 13, wherein said organic layer comprises:

R$^2$OCH$_2$CH$_2$(OCH$_2$CH$_2$)$_u$(CH$_2$)$_v$S—, in which
   R$^2$ is a member selected from the group consisting of H, alkyl, acyl and recognition moieties;
   u is a number between 1 and 50; and
   v is a number between 0 and 20.

21. The material according to claim 20, wherein R$^2$ is a member selected from H and $CH_3$.

22. The material according to claim 20, wherein u is a number between 5 and 20.

23. The material according to claim 13, wherein said organic layer forms a self-assembled monolayer.

24. The material according to claim 1, wherein said organosulfur layer comprises a moiety that undergoes a change in state upon exposing said moiety to an external agent.

25. The material according to claim 24, wherein said external agent is a member selected from the group consisting of light, electrical field, magnetic field, heat, change in fluid pH, change in fluid ionic strength and combinations thereof.

26. The material according to claim 1, wherein said recognition moiety is a member selected from the group consisting of biomolecules, organic groups, metal chelates and organometallic moieties.

27. The material according to claim 26, wherein said organic group is a member selected from the group consisting of amines, sulfonamides, quaternary phosphonium, tertiary sulfonium, acids, drugs, chelating agents, crown ethers, cyclodextrins and combinations thereof.

28. The material according to claim 27, wherein said amine is a member selected from the group consisting of quaternary amines, heterocyclic amines and combinations thereof.

29. The material according to claim 27, wherein said acid is a member selected from the group consisting of sulfonic acids, carboxylic acids, phosphonic acids and combinations thereof.

30. The material according to claim 26, wherein said biomolecule is a member selected from the group consisting of antibodies, antigens, carbohydrates, nucleic acids, peptides, enzymes and receptors.

31. A multilayered porous membrane comprising:
    (a) a porous polycarbonate track-etched substrate;
    (b) a metal film adhered onto said substrate; and
    (c) an organic layer attached to said metal film, said organic layer having a recognition moiety attached thereto
wherein said membrane is porous.

32. The material according to claim 31, wherein said metal film is a member selected from the group consisting of nickel film, copper film, silver film, gold film, platinum film, palladium film and combinations thereof.

33. The material according to claim 31, wherein said organic layer comprises a group having the structure:

$$—SR^1(X^1)_n$$

wherein
   $R^1$ is a linking group between sulfur and $X^1$;
   $X^1$ is a recognition moiety;
   n is a number between 1 and 50.

34. The material according to claim 33, wherein $R^1$ is a member selected from the group consisting of alkyl and substituted alkyl groups.

35. The material according to claim 31, wherein said recognition moiety is a member selected from acids and amines.

36. The material according to claim 35, wherein said amine is a member selected from quaternary amines, heterocyclic amines and combinations thereof.

37. The material according to claim 35, wherein said acid is a member selected from the group consisting of carboxylic acids, sulfonic acids, phosphonic acids and combinations thereof.

38. A multilayered porous ion exchange membrane comprising:
    (a) a porous substrate;
    (b) a metal film adhered onto said substrate; and
    (c) an organic layer attached to said metal film, said organic layer comprising a recognition moiety that binds or repels an ion
wherein said membrane is porous.

39. The material according to claim 38, wherein said substrate is a member selected from the group consisting of metals, inorganic oxides, inorganic glasses, organic polymers and combinations thereof.

40. The material according to claim 39, wherein said organic polymer is a member selected from the group consisting of polypropylene, nylon, fluorocarbon, polyester, polyethylene, polysulfone, polyether sulfone, cellulose, cellulose ester, ethyl vinyl acetate, polycarbonate, polyaramide, polyimide and combinations thereof.

41. The material according to claim 39, wherein said metal is a member selected from the group consisting of nickel, copper, silver, gold, platinum, palladium and combinations thereof.

42. The material according to claim 39, wherein said inorganic oxide is a member selected from the group consisting of ZnO, TiO$_2$, Fe$_2$O$_3$, Al$_2$O$_3$, CeO$_2$, SnO$_2$, CuO, Cr$_2$O$_3$, SiO$_2$ and combinations thereof.

43. The material according to claim 38, wherein said substrate is track-etched.

44. The material according to claim 38, wherein said metal film is a member selected from the group consisting of nickel film, copper film, silver film, gold film, platinum film, palladium film and combinations thereof.

45. The material according to claim 44, wherein said metal film is a gold film.

46. The material according to claim 38, wherein said metal film is layered onto said substrate by electroless deposition.

47. The material according to claim 38, wherein said organic layer is attached to said metal film through a mechanism which is a member selected from the group consisting of covalent bonding, ionic bonding, coordination, van der Waals interactions, chemisorption, physisorption and combinations thereof.

48. The material according to claim 38, wherein said organic layer comprises an organosulfur moiety.

49. The material according to claim 48, wherein said organosulfur layer comprises a moiety that undergoes a change in conformation upon exposing said moiety to a member selected from the group consisting of light, heat or combinations thereof.

50. The material according to claim 48, wherein said organic layer comprises a group having the structure:

$$—SR^1(X^1)_n$$

wherein
   $R^1$ is a linking group between sulfur and $X^1$;
   $X^1$ is a recognition moiety; and
   n is a number between 1 and 50.

51. The material according to claim 50, wherein $R^1$ is a member selected from the group consisting of stable linking groups and cleaveable linking groups.

52. The material according to claim 51, wherein $R^1$ is a stable linking group which is a member selected from the group consisting of alkyl, substituted alkyl, aryl, arylalkyl, substituted aryl, substituted arylalkyl, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups.

53. The material according to claim 52, wherein $R^1$ is a member selected from the group consisting of alkyl and substituted alkyl groups.

54. A method of producing a multilayered porous membrane comprising:
    (a) contacting a porous substrate with a metal plating solution to form a porous substrate having a metal film adhered thereto;
    (b) contacting said metal coated substrate from step (a) with a solution comprising nitric acid, thereby activating said metal film;
    (c) contacting said metal coated substrate from step (b) with a plurality of organic molecules that associate with the activated metal film, thereby forming an organic layer on said particle, wherein at least a portion of said plurality of organic molecules comprise a member selected from the group consisting of recognition moieties, reactive groups, protected reactive groups and combinations thereof
wherein said membrane is porous.

55. The material according to claim 54, wherein said metal plating solution comprises a member selected from the group consisting of nickel, copper, silver, gold, platinum, palladium and combinations thereof.

56. The method according to claim 55, wherein said plating solution comprises a reducible gold salt.

57. The method according to claim 56, wherein said sensitizer is a transition metal salt.

58. The method according to claim 57, wherein said transition metal salt is a salt of $Sn^{+2}$.

59. The method according to claim 56, wherein said gold plating solution comprises a reducible gold salt.

60. The method according to claim 59, wherein said gold plating solution further comprises a reducing agent.

61. The method according to claim 60, wherein said reducing agent is formaldehyde.

62. The method according to claim 59, wherein said reducible gold salt is $Na_3Au(SO_3)_2$.

63. The method according to claim 54, further comprising, prior to step (a), contacting a particulate substrate with a sensitizer to form a sensitized particulate substrate.

64. The method according to claim 54, further comprising, prior to step (a), contacting said sensitized particulate substrate with a silver solution to form a silver coated particle.

65. The method according to claim 64, wherein said silver solution comprises $AgNO_3$.

66. The method according to claim 64, wherein said silver solution further comprises ammonia.

67. The method according to claim 54, wherein said plurality of organic molecules comprises an organosulfur.

68. The method according to claim 54, wherein said plurality of organic molecules comprises a moiety selected from the group consisting of recognition moieties, reactive moieties, protected reactive moieties and combinations thereof.

69. The method according to claim 68, wherein said plurality of organic molecules comprises a reactive moiety and said method further comprises:

(d) reacting said reactive moiety with a recognition moiety.

70. The method according to claim 68, wherein said plurality of organic molecules comprises a protected reactive moiety and said method further comprises:

(d) deprotecting said protected reactive moiety to form a reactive moiety;

(e) reacting said reactive moiety with a recognition moiety.

71. A drug delivery device comprising:

(a) a porous substrate;

(b) a metal film adhered onto said substrate;

(c) an organic layer attached to said metal film, said organic layer comprising a recognition moiety; and (d) a drug moiety reversibly associated with said recognition moiety.

* * * * *